United States Patent [19]

Rao et al.

[11] Patent Number: 5,628,310

[45] Date of Patent: May 13, 1997

[54] METHOD AND APPARATUS TO PERFORM TRANS-CUTANEOUS ANALYTE MONITORING

[75] Inventors: Govind Rao; Henryk Szmacinski, both of Baltimore, Md.; Joseph R. Lakowicz, 10037 Fox Den Rd., Ellicott City, Md. 21042

[73] Assignee: Joseph R. Lakowicz, Baltimore, Md.

[21] Appl. No.: 444,927

[22] Filed: May 19, 1995

[51] Int. Cl.$^6$ .................................................. A61B 5/00
[52] U.S. Cl. ........................................................... 128/633
[58] Field of Search ........................ 128/632, 633, 128/635; 604/890.1, 891.1, 19, 20, 21; 204/403, 415

[56] References Cited

U.S. PATENT DOCUMENTS

| | | |
|---|---|---|
| 4,321,057 | 3/1982 | Buckles . |
| 4,399,099 | 8/1983 | Buckles . |
| 4,401,122 | 8/1983 | Clark, Jr. . |
| 4,557,900 | 12/1985 | Heitzmann . |
| 4,580,059 | 4/1986 | Wolfbeis et al. . |
| 4,632,807 | 12/1986 | Marsoner et al. . |
| 4,657,736 | 4/1987 | Marsoner et al. . |
| 4,661,367 | 4/1987 | Forse et al. . |
| 4,704,029 | 11/1987 | Van Heuvelen ................ 128/633 |
| 4,752,115 | 6/1988 | Murray, Jr. et al. . |
| 4,994,396 | 2/1991 | Lefkowitz et al. . |
| 5,043,286 | 8/1991 | Khalil et al. . |
| 5,047,350 | 9/1991 | Switalski . |
| 5,101,814 | 4/1992 | Palti ................................ 128/635 |
| 5,173,432 | 12/1992 | Lefkowitz et al. . |
| 5,184,618 | 2/1993 | Wider et al. . |
| 5,190,041 | 3/1993 | Palti ................................ 128/635 |
| 5,272,088 | 12/1993 | Morlotti . |
| 5,272,090 | 12/1993 | Gavish et al. . |
| 5,284,139 | 2/1994 | Khalil et al. . |
| 5,311,013 | 5/1994 | Gutcheck et al. . |
| 5,342,789 | 8/1994 | Chick . |
| 5,368,028 | 11/1994 | Palti ................................ 128/635 |

OTHER PUBLICATIONS

"Phase Fluorometric Sterilizable Optical Oxygen Sensor" by Shabbir B. Bambot et al, *Biotechnology and Bioengineering*, vol. 43, pp. 1139–1145 (1994).

"Fibre–Optic Oxygen Sensor With The Fluorescence Decay Time as the Information Carrier" by Max E. Lippitsch et al, *Analytica Chimica Acta*, 205 (1988).

"Sensing Oxygen Through Skin Using a Red Diode Laser and Fluorescence Lifetimes" by Shabbir B. Bambot et al. *Biosensors & Bioelectronics*, vol. 10, No. 67 (1995).

"Potential Applications of Lifetime–Based, Phase–Modulation Fluorimetry in Bioprocess and Clinical Monitoring" by Shabbir B. Bambot et al, *TIBTECH* Mar. 1994 (vol. 13) pp. 106–115.

*Primary Examiner*—Lee S. Cohen
*Assistant Examiner*—Eric F. Winakur
*Attorney, Agent, or Firm*—Gary M. Nath; Nath & Associates

[57] ABSTRACT

An apparatus and method to enable minimally invasive transdermal measurements of the fluorescence lifetime of an implanted element without reagent consumption and not requiring painful blood sampling. The monitoring apparatus displays the quantity of a selected substance present in the skin and stores the data in memory. The stored information can be transmitted via modem, or antenna, to a master station for diagnostic purposes or clinical evaluation. The use of this method and apparatus improves control of blood monitoring, and therefore, enhances long-term disease management with fewer complications.

33 Claims, 9 Drawing Sheets

○ No intralipid
● In intralipid vs. excitation source
■ In intralipid vs. fluorescent dye

METHOD AND APPARATUS TO PERFORM TRANS-CUTANEOUS ANALYTE MONITORING

The U.S. Government has a paid-up license in this invention and the right in limited circumstance to require the patent owner to license others on reasonable terms as provided by the terms of Grant No. BES-9413262 awarded by the National Science Foundation and Grant Nos. RR-08199 and RR-07510 awarded by the National Institute of Health.

BACKGROUND OF THE INVENTION

1. Field of the Invention

The present invention pertains to an apparatus and method to enable minimally invasive trans-cutaneous measurements of the fluorescence of an implanted element without reagent consumption and not requiring invasive sampling. The procedure is completely non-invasive after one implant. The monitoring apparatus displays the quantity of a selected substance present in the skin and stores the data in memory. The stored information can be transmitted via modem, or antenna, to a master station for diagnostic purposes or clinical evaluation. The use of this method and apparatus improves control of blood monitoring, and therefore, enhances long-term disease management with fewer complications.

2. Description of the Prior Art

Instruments capable of continuously indicating the chemical composition of blood have proved to be useful in regulating operative and postoperative managements of patients, in teaching and research. At first, such instruments were used with sensors mounted directly in the extracorporeal blood circuit that is used for perfusion of open-heart surgery patients. Later, continuous monitoring of both machine and patients was conducted by means of continuous withdrawal of blood pumped into external cuvettes equipped with appropriate sensors, or by use of implantation of arterial catheters.

Other techniques have been employed for measuring biological substances in the blood. For instance, ethanol is currently measured in blood, either directly or by a breath sampling, by classical chemical, gas chromatographic and enzyme methods. One of the alcohol enzyme methods depends upon the polarographic measurement of hydrogen peroxide, while others depend upon the consumption of oxygen.

The continuous monitoring of blood oxygen by a heated electrode positioned on hyperemic skin has been accomplished. Substances such as halogenated organic compounds, particularly fluorinated compounds, have also been found to diffuse through the skin and have been measured.

Other methods for cutaneously measuring substances in the blood include contacting the substrate through the skin of a mammal with an enzyme selective for the substrate being analyzed, then reacting the substrate with the enzyme and directly detecting a condition of the skin as a measure of the amount of substrate.

The following are representative of the prior art systems available:

Wider et al., U.S. Pat. No. 5,184,618 discloses a system for invasively measuring blood gas parameters, such as pH, $pO_2$ or $pCO_2$, or for measuring other parameters influencing the time constant of the excited state of a fluorescent dye and a correlation between the respective values of the blood gas parameter and the associated values of the time constant of the fluorescent measuring probe.

Murray Jr. et al., U.S. Pat. No. 4,752,115, discloses a device for sensing oxygen, particularly for use in medical applications. The device includes an optical waveguide and an oxygen sensing medium disposed on the waveguide. The sensing medium fluoresces in response to light from a light source such that the intensity of fluorescence is dependent on the partial pressure of oxygen in the environment. The sensing medium includes an oxygen sensitive fluorescent dye in a matrix consisting of a plasticized polymer.

Lefkowitz et al., U.S. Pat. No. 4,994,396, discloses a sensor and a method for determining the concentration or the partial pressure of oxygen comprising (a) means for transmitting and collecting light to and from a light modifying medium; and (b) a light modifying medium containing a luminescent dye dispersed in or upon a matrix and the dye is accessible to oxygen, wherein said luminescent dye contains a hexanuclear core of molybdenum, tungsten or mixtures thereof having coordination sites, wherein each coordination site is occupied by a ligand.

Khalil et al., U.S. Pat. No. 5,043,286 discloses methods of and luminescent substances for measuring oxygen concentration of a test fluid. A test fluid is contacted with a plastic film containing a luminescent substance, the luminescent emission intensity of which is quenched in the presence of oxygen. The film is subjected to irradiation by light that is strongly absorbed by the luminescent substance, and a measure of the time dependence of luminescent emission intensity I(t) is obtained. Three modes of measuring quenching, and thus the oxygen concentration, from I(t) are described.

Khalil et al., U.S. Pat. No. 5,284,159, discloses a method for converting a value for the partial pressure of oxygen ($pO_2$) in blood at a measurement temperature to a corresponding value at a reference temperature (37° C.). A value for $pO_2$ is determined by measurements made in a patient's blood stream using a phosphorescent compound that is sensitive to the concentration of oxygen. The phosphorescent compound is illuminated with short pulses of light, causing it to produce a phosphorescent emission having a rate of decay that varies as the function of the partial pressure of oxygen in the blood surrounding the phosphorescent compound. A detector produces an electrical signal corresponding to the intensity of the phosphorescent emission, and the electrical signal is converted to a corresponding digital value for input to a microcomputer. Also supplied to the microcomputer in digital form is a signal indicative of the temperature at the measurement site where the phosphorescent compound is disposed. The microcomputer determines the phosphorescent decay rate and from that value, determines the $pO_2$ at the measurement site for the temperature at which the measurement was made. An initial estimate of a corresponding value for $pO_2$ at the reference temperature is made as a function of the measurement temperature and the $pO_2$ at that temperature.

Wolfbeis et al., U.S. Pat. No. 4,580,059, teaches the simultaneous measurement of the concentrations of several substances. A number of fluorescence measurements corresponding to the number of substances to be tested are performed using at least one fluorescent indicator which is non-specific relative to at least one of the substances to be tested. Each florescent indicator has different quenching constants with regard to the individual substances quenching its intensities. From the known, unquenched fluorescence intensities of the fluorescent indicators employed, the quenched fluorescence intensities obtained by measuring, and from the quenching constants that are known, or rather, have been determined beforehand by graphical methods or calculation, the concentrations and/or concentration ratios of the individual substances are obtained.

Clark, U.S. Pat. No. 4,401,122, discloses cutaneous methods for measuring substrates in mammalian subjects. A condition of the skin is used to measure a number of important substances which diffuse through the skin or are present underneath the skin in the blood or tissue. According to the technique, an enzyme whose activity is specific for a particular substance or substrate is placed on, in or under the skin for reaction. The condition of the skin is then detected by suitable means as a measure of the amount of the substrate in the body. For instance, the enzymatic reaction product or by-product of the reaction is detected directly through the skin as a measure of the amount of substrate. Polarographic electrodes or enzyme electrodes are employed as skin-contact analyzers in the transcutaneous measurement of oxygen or hydrogen peroxide to quantitatively detect substances such as glucose and alcohol. In a preferred quantitative technique, the skin is arterialized, i.e. heated or otherwise treated to arterialize the skin capillaries when the measurements are made. Colorimetric detection methods are also employed.

Among the various clinical measurements, the determination of blood gases (pH, $pCO_2$, $pO_2$) is one of the most important. Blood gases are routinely performed on patients in the Critical Care Unit. At present, such measurements are performed mostly by classical methods, such as gas chromatography and pH electrode, which are usually located in a central laboratory.

It is difficult to obtain the blood gas report in less than 30 minutes, by which time the patient's status is often quite different. Additionally, handling of blood by health-care workers is undesirable with regard to the risk of AIDS and other infectious diseases. At present, determination of blood gases is time-consuming and expensive, with a cost of at least $400,000,000 per year in the United States.

As can be seen by the above, there are a variety of techniques available for the measurement of blood gases and other substances. However a new apparatus and method are desired which can provide non-invasive continuous monitoring, immediate data availability, the ability to automatically save and transmit data for analysis, and can be used as part of a coordinated health monitoring system.

SUMMARY OF THE INVENTION

A preferred embodiment of the trans-cutaneous analyte monitor comprises, a light emitting means for emitting an excitation light having predetermined wavelength and temporal characteristics; a bio-compatible implant, said bio-compatible implant emitting fluorescence having predetermined wavelength and temporal characteristics upon absorption of said excitation light emitted from said light emitting means; a detector means to detect said fluorescence from said bio-compatible implant, said detector means producing an electrical signal proportional to said fluorescence; a comparison means to compare said wavelength and temporal characteristics of said light emitted from said light emitting means and said wavelength and temporal characteristics of said fluorescence from said bio-compatible implant said comparison means receiving input from said light emitting means and said detector means and having an output; and a computing means to receive said output of said comparison means and relating said comparison of said wavelength and temporal characteristics of said light emitted from said light emitting means and said wavelength and temporal characteristics of said fluorescence from said bio-compatible skin implant to the quantity of a biologically significant substance present.

Another preferred embodiment of this invention comprises, said predetermined wavelength and temporal characteristics of said fluorescence being altered by collisional quenching caused by the presence of a predetermined biologically significant substance.

Another preferred embodiment of this invention comprises, said comparison means to compare said wavelength and temporal characteristics of said light emitted from said light emitting means and said wavelength and temporal characteristics of said fluorescence from said bio-compatible implant is by means of intensity based sensing, and wherein said comparison means to compare said wavelength and temporal characteristics of said light emitted from said light emitting means and said wavelength and temporal characteristics of said fluorescence from said bio-compatible implant is by means of lifetime-based sensing.

In another preferred embodiment said bio-compatible implant comprises a fluorescent donor and analyte-dependent acceptor which spectrally overlaps said fluorescent donor, said bio-compatible implant emitting fluorescence of a predetermined wavelength and temporal characteristics upon absorption of said excitation light emitted from said light emitter, said fluorescence wavelength and temporal characteristics being altered when a predetermined biologically significant substance is present and said comparison means to compare said wavelength and temporal characteristics of said light emitted from said light emitting means and said wavelength and temporal characteristics of said fluorescence from said bio-compatible implant is by means of intensity based sensing.

In another preferred embodiment said bio-compatible implant comprises a fluorescent donor and analyte-dependent acceptor which spectrally overlaps said fluorescent donor, said bio-compatible implant emitting fluorescence of a predetermined wavelength and temporal characteristics upon absorption of said excitation light emitted from said light emitter, said fluorescence wavelength and temporal characteristics being altered when a predetermined biologically significant substance is present and said comparison means to compare said wavelength and temporal characteristics of said light emitted from said light emitting means and said wavelength and temporal characteristics of said fluorescence from said bio-compatible implant is by means of lifetime-based sensing.

In another preferred embodiment said bio-compatible implant comprises an analyte-free and analyte-bound form of a fluorescent emitter and wherein the ratio of the signals at two excitation or emission wavelengths is used for quantitative measurements of a predetermined biologically significant substance and said comparison means to compare said wavelength and temporal characteristics of said light emitted from said light emitting means and said wavelength and temporal characteristics of said fluorescence from said bio-compatible implant is by means of intensity based sensing.

In another preferred embodiment said bio-compatible implant comprises an analyte-free and analyte-bound form of a fluorescent emitter and wherein the ratio of the signals at two excitation or emission wavelengths is used for quantitative measurements of a predetermined biologically significant substance and said comparison means to compare said wavelength and temporal characteristics of said light emitted from said light emitting means and said wavelength and temporal characteristics of said fluorescence from said bio-compatible implant is by means of lifetime-based sensing.

Yet another preferred embodiment of the trans-cutaneous analyte monitor comprises, a light emitting means for emitting an excitation light having predetermined wavelength and temporal characteristics; a bio-compatible implant, said bio-compatible implant emitting fluorescence having predetermined wavelength and temporal characteristics upon absorption of said excitation light emitted from said light emitting means; a detector means to detect said fluorescence from said bio-compatible implant wherein said detector measures the wavelength and temporal characteristics of said bio-compatible skin implant fluorescence, and further wherein said detector emits an electrical signal which is directly proportional to the fluorescence wavelength and temporal characteristics received; a comparison means to compare said wavelength and temporal characteristics of said light emitted from said light emitting means and said wavelength and temporal characteristics of said fluorescence from said bio-compatible implant; a computing means to relate said comparison of said wavelength and temporal characteristics of said intensity modulated light emitted from said light emitting means and said wavelength and temporal characteristics of said fluorescence from said bio-compatible skin implant to the quantity of a biologically significant substance present; a display means for displaying said quantity of biologically significant substances; a memory storage device for receiving said output of said computing means; and a data transfer means, said data transfer means receiving input from said memory storage device and whereby said quantity of said biologically significant substance present stored in said memory storage device.

Another preferred embodiment of the trans-cutaneous analyte monitor comprises a frequency synthesizer, wherein said frequency synthesizer produces a modulated electrical output, wherein said light emitting means receives said modulated electrical output of said frequency synthesizer causing said light emitter to emit an intensity modulated excitation light of predetermined wavelength and temporal characteristics, and wherein said detector measures the wavelength and temporal characteristics of said bio-compatible implant fluorescence, and further wherein said detector emits an electrical signal which is directly proportional to the fluorescence wavelength and temporal characteristics received and wherein said comparison means compares the phase angle difference between said excitation light predetermined wavelength and temporal characteristics and said wavelength and temporal characteristics of said bio-compatible fluorescence, and wherein said computing means computes the quantity of said biologically significant substance present from said comparison of said light emitted from said light emitting means and said wavelength and temporal characteristics of said fluorescence from said bio-compatible implant and wherein said light emitting means is a light emitting diode.

A preferred method to trans-cutaneously monitor analytes comprises, emitting a modulated excitation light from a light emitting means, said excitation light having predetermined wavelength and temporal characteristics; implanting a bio-compatible implant, said implant emitting fluorescence having predetermined wavelength and temporal characteristics upon absorption of said excitation light emitted from said light emitting means; detecting said fluorescence wavelength and temporal characteristics from said bio-compatible implant; comparing said wavelength and temporal characteristics of said excitation light emitted from said light emitting means and said wavelength and temporal characteristics of said fluorescence from said bio-compatible implant; and computing said wavelength and temporal characteristics of said light emitted from said light emitting means and said wavelength and temporal characteristics of said fluorescence from said bio-compatible implant to quantify the amount of a biologically significant substance present under the skin.

Another preferred method comprises displaying said quantity of biologically significant substance, storing in a memory storage device said output of said computing means, transferring said data from said memory storage device to a remote receiving station.

Another preferred method is wherein said bio-compatible implant comprises a fluorophore wherein said bio-compatible implant emits fluorescence of a predetermined wavelength and temporal characteristics, said fluorescence of a predetermined wavelength and temporal characteristics being altered by collisional quenching caused by the presence of a predetermined biologically significant substance.

In another preferred method said bio-compatible implant comprises an analyte-free and analyte-bound form and wherein the ratio of the signals at two excitation or emission wavelengths is used for quantitative measurements.

Another preferred method comprises a fluorescent donor and analyte-dependent acceptor which spectrally overlaps said fluorescent donor, said bio-compatible implant emitting fluorescence of a predetermined wavelength and temporal characteristics upon absorption of said excitation light emitted from said light emitter, said fluorescence wavelength and temporal characteristics being altered when a predetermined biologically significant substance is present.

Yet another preferred method comprises synthesizing a modulated electrical output by means of a frequency synthesizer; inputting said modulated electrical output of said frequency synthesizer means into a light emitting means whereby said light emitting means emits an intensity modulated excitation light, said excitation light having predetermined wavelength and temporal characteristics; implanting a bio-compatible implant wherein said bio-compatible implant emits fluorescence of a predetermined wavelength and temporal characteristics upon absorption of said excitation light emitted from said light emitter, said fluorescence wavelength and temporal characteristics being altered when a predetermined biologically significant substance is present; detecting said bio-compatible implant emitting fluorescence of a predetermined wavelength and temporal characteristics by detection means wherein said detection means emits an electrical signal which is directly proportional to the fluorescence wavelength and temporal characteristics received; comparing said wavelength and temporal characteristics of said excitation light emitted from said light emitting means and said wavelength and temporal characteristics of said fluorescence from said bio-compatible implant; computing the phase angle difference between said comparison of said light emitted from said light emitting means and said wavelength and temporal characteristics of said fluorescent light from said bio-compatible skin implant to the quantity of said biologically significant substance present and relating said phase angle difference to the quantity of a biologically significant substance present; and displaying the quantity of said biologically significant substance present.

DETAILED DESCRIPTION OF THE PREFERRED EMBODIMENT

Figure 1:
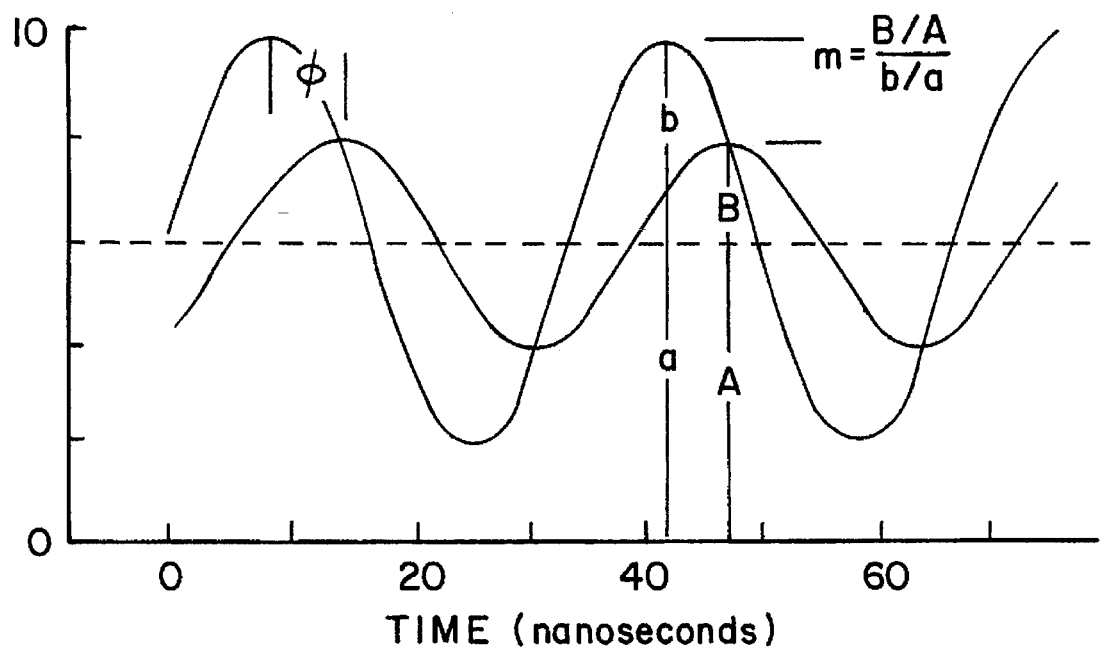
FIG. 1 is a graph depicting lifetime-based (frequency domain) phase-modulation.

There are two common types of illumination detection sensor systems: absorption and luminescent. The present invention is used in conjunction with a luminescent system, of which there are two types: phosphorescent and fluorescent. Such systems operate on the concept of measuring the radiation emitted by the excitation of a substance.

Optical sensors, particularly fluorescence sensors, offer advantages over electrochemical sensors. These include the absence of electrical interferences (magnetic or electrical fields), no analyte consumption, the possibility of multiple measurements using optical fibers and the possibility of miniaturization. Fiber-optics can be readily adapted for chemical sensing and be fabricated as miniature devices suitable for remote sensing and safe operation in chemical environments. Perhaps more importantly, optical detection of analytes can be accomplished without the use of radioactive tracers, and can minimize the need for sample handling and manipulation. Fluorescence sensing provides the additional advantage of good sensitivity, with the specificity being obtained from either the properties of the fluorophore or its fabrication within the sensing element.

At present, most fluorescence sensors are based on intensity measurements, that is, intensity-based sensing, in which the change of intensity in response to the analyte of interest is measured. These intensity changes can be due to changes in extinction coefficient due to probe ionization, changes in quantum yield of the probe upon analyte binding, or due to inner filtering resulting from the optical density changes of indicators.

The fluorescence intensity measurement depends on the intensity of exciting light, the extinction coefficient and concentration of the probe, the optical density at the excitation and the emission wavelengths, the optical path length, the fluorescence quantum yield of the probe, and the detector sensitivity. The fluorescence intensity can also vary due to light scattering and/or absorption characteristics of the sample.

An alternate fluorescent sensor measurement is fluorescent lifetime. The fluorescence lifetime of a sample is the mean duration of time the fluorophore remains in the excited state. Following pulsed excitation, the intensity decays of many fluorophores are single exponential $$I(t)=I_o exp(-t/\tau),\qquad(1)$$

where $I_o$ is the intensity at t=0, and τ is the lifetime. A variety of molecular interactions can influence the decay time. The excited fluorophore can return to the ground state by the radiative (emission) pathway with a rate $k_r$. The inverse of this rate constant ($\tau_r=k_r^{-1}$) is usually called the intrinsic or radiative lifetime. The radiative decay rate $k_r$ is generally of intramolecular origin, with only a modest dependence on the local environment. There are several formulas to calculate radiative decay rate using the absorption and emission spectra. The simplest of them requires only integration of the first absorption band $$k_r=2900n^2\bar{v}_0^{-2}\int\epsilon(\bar{v})d\bar{v},\qquad(2)$$

where n is the refractive index of the solvent, $\bar{v}_0$ the wavenumber of the maximum of the absorption band, and $\epsilon(\bar{v})$ in the wavenumber-dependent extinction coefficient. The approximate value of $k_r$ can be estimated from a simplified form of Eq. (2), $k_r=10^4\epsilon_{max}$. Upon binding the analyte the absorption spectrum of the probe in many cases changes (spectral shift and/or change in extinction coefficient), which can result in changes the radiative decay rate and thus affect the fluorescence decay time.

The measured fluorescence lifetime τ is usually shorter than the radiative lifetime $\tau_r$ because of presence of other decay rates which can be dependent on intramolecular processes and intermolecular interactions. The measured fluorescence lifetime (τ) is given by the inverse of the total rate of dynamic processes that cause deactivation from the excited (mostly singlet $S_1$) state $$\tau=\frac{1}{k_r+k_{nr}+k_Q[Q]+k_T}.\qquad(3)$$

Non-radiative processes ($k_{nr}$) can occur with a wide range of rate constants. Molecules with high $k_{nr}$ values display low quantum yields due to rapid depopulation of the excited state by this route. The measured lifetime in the absence of collisional or energy transfer quenching is usually referred to as $\tau_0$, and is given by $$\tau_0=(k_r+k_{nr})^{-1}.$$

There are two widely used methods to measure the fluorescence decay time. These are the pulse or time-domain method and the phase-modulation or frequency-domain method. In the pulse method, one excites the sample with a brief pulse of light, typically shorter than the fluorescence decay time, followed by measurement of the time-dependent decay of the emission. The lifetime can be calculated from the rate of decay. An alternative method is to excite the sample with an intensity modulated light source. The lifetime is then determined by the phase shift of the emission relative to the phase of the incident light. The lifetime can also be determined from the relative modulation of the emission compared to the modulation of the incident light.

Due to the absorption of the fluorescence by the acceptor the donor emission displays a phase angle shift in relation to the excitation, which is dependent on the analyte concentration around the sensor. This is illustrated in FIG. 1. The excitation and emission are modulated at the same circular frequency ($\omega=2\pi\times$frequency in Hz). The emission is delayed by the phase angle ($\Phi$). The relative amplitude of the variable portion of the emission (B/A) is smaller than that of the excitation (b/a). The phase angle ($\Phi$) can be used to calculate the lifetime of the fluorophore. The demodulation factor [$m=(Ba/bA)$] can also be used to independently calculate the lifetime ($\tau$) using the equations, which is valid for a single exponential decay:

$$\tan\Phi=\omega\tau \text{ and } m=[1+\omega^2\tau^2]^{-\frac{1}{2}} \tag{4}$$

These phase values are correlated to acceptor concentrations. Values or data at several frequencies can be taken, increasing the precision and/or reliability of the measurements.

Another characteristic of lifetime-based sensing is the absolute nature of the measurement and after a one-time calibration, the sensor never needs recalibration. This feature is ideal for an implanted sensor.

The electronics for phase-modulation sensing can be based on relatively low-cost components, and phase and modulation at a single frequency are easily measured in a second or less of data acquisition.

The following is a discussion of various means of detecting fluorescent intensity and lifetime-based changes based on the physical mechanisms causing the changes. One mechanism for creating changes is collisional quenching. A variety of substances act as quenchers, including oxygen, nitrous oxide, heavy atoms, Cl$^-$, and amines, to name a few. By consideration of the lifetime in the absence ($\tau_0$) and presence ($\tau$) of collisional quenchers (no resonance energy transfer), one can easily see that such quenching decreases the lifetime of the excited state $$\frac{\tau_0}{\tau}=1+\tau_0 k_q[Q], \tag{5}$$

where $k_q$ is the biomolecular quenching constant. In fluid solution with efficient quenchers $k_q$ is typically in the range of $10^9$ to $10^{10}$ M$^{-1}$sec$^{-1}$. Collisional quenching by oxygen can be used for intensity-based and lifetime-based sensing of oxygen using the long-lifetime transition metal complexes resulting with large amount of quenching by oxygen. Collisional quenching also results in the transfer of electrons which are induced by excitation. Binding of cations prevents electron transfer from the electron-donating group, thus preventing intramolecular quenching, resulting in an enhancement of quantum yield upon binding metal cations without observable spectral shifts.

Another mechanism which decreases the fluorescence intensity and decay time is fluorescence resonance energy transfer (FRET). An energy-transfer-based sensor consists of two kinds molecules. Donors can be selected for excitability with inexpensive light sources. Acceptors are selected with an analyte-dependent absorbance that spectrally overlaps the donor fluorescence when added to the sensor. Fluorescent resonance energy transfer (FRET) from the donor to the acceptor will quench the fluorescence and alter both the fluorescence intensity and lifetime. By using the phenomena of fluorescent resonance energy transfer (FRET), the donor need not be sensitive to a particular analyte, and the acceptor does not need to be fluorescent. This energy transfer takes place without the appearance of a photon, and the transfer rate depends primarily on the extent of overlap of the emission spectrum of the donor with that of the absorption spectrum of the acceptor, and the distance between the two.

An advantage of using fluorescent resonance energy transfer (FRET) as the transduction mechanism is that this interaction can be reliably predicted to occur for any Donor-Acceptor pair displaying suitable spectral overlap. Consequently, Donor-Acceptor pairs may be selected which are suitable for sensing in tissues, which are excited with simple light sources, and which are advantageous for simplicity in design and robustness. While the signal levels will be attenuated by tissue absorption and/or scatter the intensity decays are not significantly perturbed. The time scale of photon migration in tissues is near 200 picoseconds. For such a sensor the donor need not be sensitive to the analyte, and the acceptor typically displays a change in absorption spectrum due to the analyte.

Yet another approach is the use of wavelength-ratiometric probes, where the ratio of signals at two excitation or emission wavelengths is used for quantitative measurements, however the ratio is independent of the probe concentration. The change in lifetime (from $\tau_F$ to $\tau_B$), characteristic of the analyte-free (F) and analyte-bound (B) forms of the probes, is due to binding of the analyte resulting in changes of the radiative and/or nonradiative decay rates. Such a probe must display different absorption and/or emission spectra when free in solution and when bound to the analyte. The absorption spectra overlap and are excited at the same wavelength. The fluorescence intensity decay of such probe is generally not a single exponential, but is given as a sum of the exponentials with decay times $\tau_F$ and $\tau_B$.

Multi-frequency phase and modulation instruments which operate at preset frequencies for a specific application are easily designed, and are well known to those skilled in the art. In detecting transcutaneous emissions, the most difficult obstacles to overcome are the absorbance and scatter of light caused by skin and the lack of fluorescent sensing probes which can be excited at wavelengths over 600 nm. Red light readily penetrates skin as diffusely scattered light. Light at 580 nm is stopped by skin absorbance, while light at 600 nm and 620 nm penetrates skin. Therefor a subcutaneous system must emit light at a wavelength greater than 600 nm and even longer wavelengths are preferred. Based on current integrated circuit designs, well known in the art, and using a diode light source, the phase fluorometer could be constructed on a single printed circuit board.

Experiment I

Figure 2:
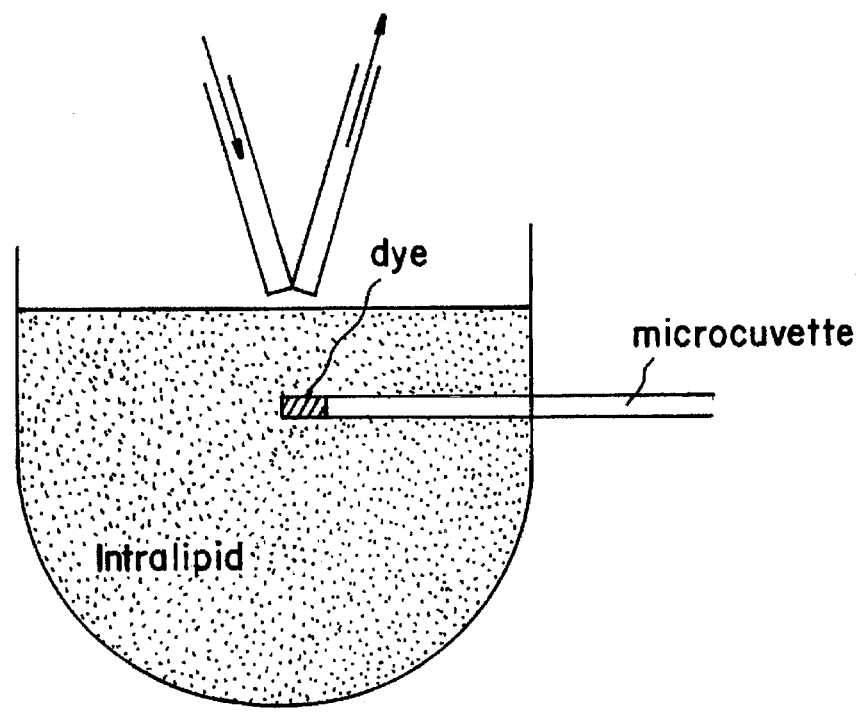
FIG. 2 Experimental geometry for lifetime-based sensing in turbid media.

We now describe how time-resolved or lifetime-based sensing is used in real-world situations, such as quasi non-invasive measurements performed through skin. The use of lifetime-based sensing in scattering media is supported by a computational study using the known scattering and absorption properties of tissues. These simulations suggested that properly referenced phase and modulation measurements can be used to recover the lifetime of fluorophores uniformly dispersed in scattering media. In FIG. 2 a sensing fluorophore is localized below the surface of the turbid media. The sensing fluorophore is contained within a capillary tube below the surface of an intralipid suspension. The microcuvette contains a fluorophore whose lifetime is sensitive to the analyte, which is pH in this instance. The measurement the pH of the "sensor" embedded in the intralipid is performed by using the time-dependent fluorescence which re-emerges from the surface of the sample. However, because there is no wavelength change with light scatter, it is not possible to selectively observe light scattered from the same region as the embedded sensor. This difficulty is circumvented by using a reference fluorophore of known decay time.

Fluorescence intensity decays were determined using the frequency-domain method. Excitation was provided by the 3.795 MHz cavity-dumped output of a Rhodamine 6G dye laser at 570 nm, or using the 75.9 MHz mode-locked output of an Argon-Ion laser at 514 nm, which provides pulse widths near 5 and 100 ps, respectively. The emission was isolated with an interference filter at 620 or 640 nm.

The sample consisted of a suspension of 20% intralipid, diluted 20-fold to 1%. The incident light was directed onto the surface of the intralipid using a 1 mm diameter fiber bundle. The emission or scattered light was collected from the surface with a similar fiber optic bundle and directed to the Photo Multiplier Tube (PMT).

The fluorescent samples were contained in about 1 mm (inner) diameter capillary tubes of the type used for melting point determinations, which allowed control of the probe's environment and knowledge of its lifetime(s). Texas Red Hydrazide (TRH) was used as a pH-insensitive reference fluorophore, and Carboxy SNARF-6 (CS6) was used as the pH lifetime sensor. Phase and modulation measurements were performed relative to scattered excitation from the surface of the intralipid at the excitation wavelength, or from the reference fluorophore at the same depth under the intralipid surface using an interference filter, to isolate the emission.

Figure 3A:
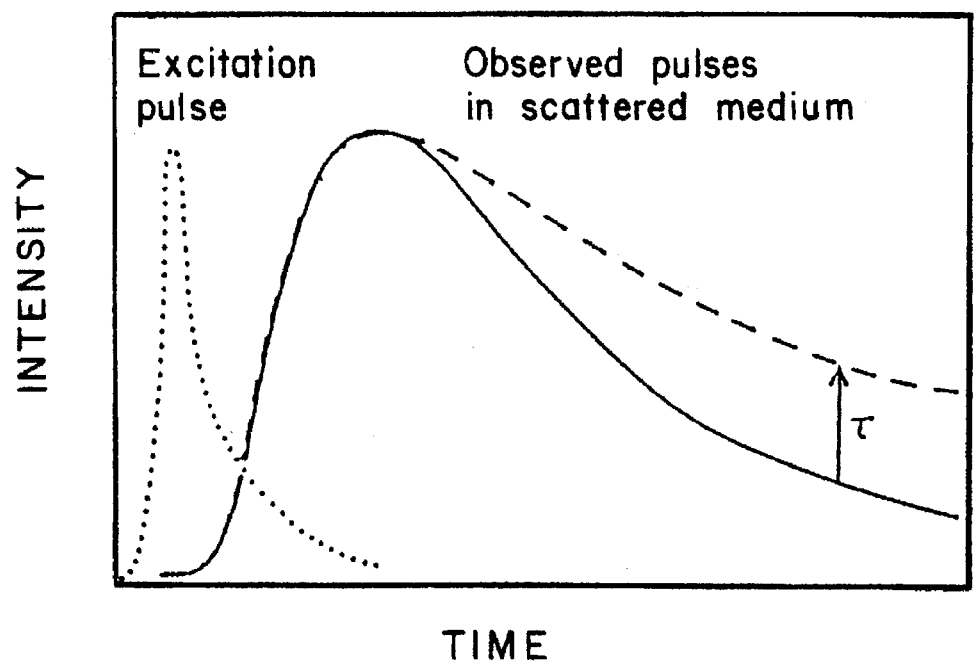
FIG. 3 Effect of multiple scattering events on time-domain (3A) or phase-modulation (3B) measurements of a fluorescence lifetime. The figure shows the pulsed or modulated excitation (. . . . .), the time-delayed scattered light (————), and the fluorescence (- - -) which is further delayed by the lifetime τ.

The frequency-domain method is used to measure the lifetimes of fluorophores in scattering media. The basis of these measurements can be understood by considering the effect of the scattering media on the time-domain data. When a sample is exposed to a δ-function pulse of light, the light pulse is time-delayed and broadened due to multiple scattering events prior to arriving at the fluorescent sensor (FIG. 3A). The broadened and time-delayed pulse excites the fluorophores, which may then decay by a single or multi-exponential decay law. The emitted light is again time-delayed and broadened as it migrates to the detector located at the surface of the sample. At the surface of the scattering media the re-emerged light (———) is time-delayed and broadened relative to the incident light (. . . . .). The fluorescence emission (- - -) is further delayed relative to the scattered light because of the lifetime τ of the excited state.

Figure 3B:
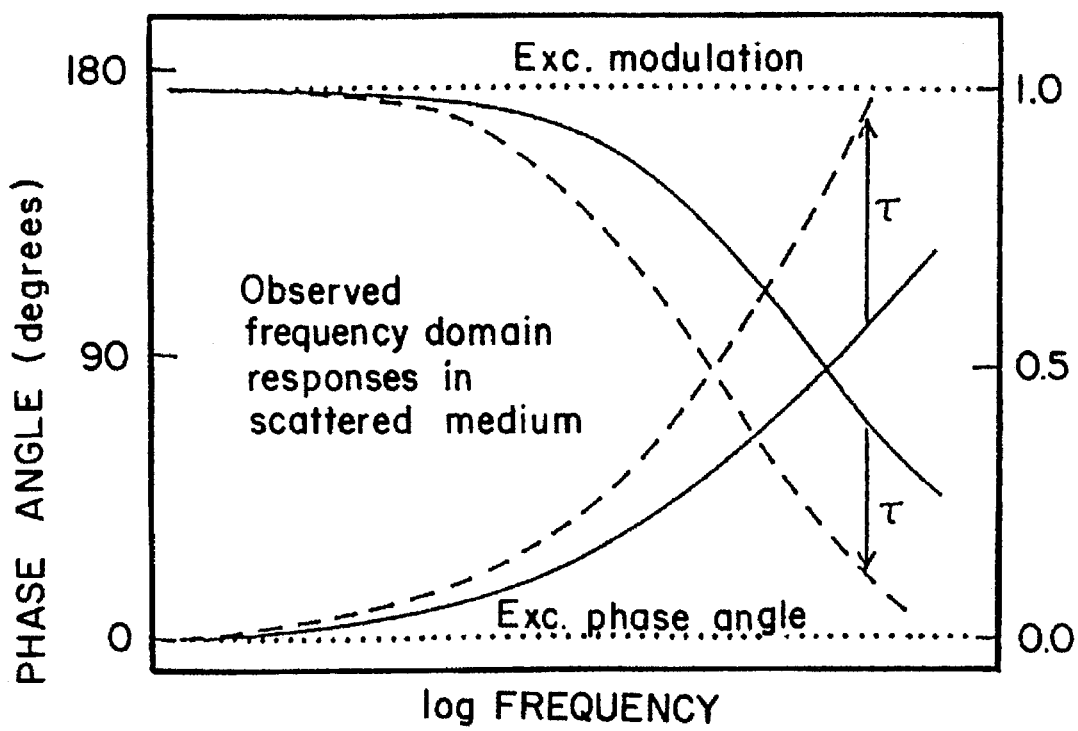

A similar effect is seen in the phase-modulation measurements (FIG. 3B). In this case, the re-emergent scattered (———) light is delayed in phase and demodulated relative to the intensity-modulated incident light (. . . . .). The re-emergent fluorescent light is further phase shifted and demodulated due to the fluorescent lifetime (- - -). Our goal is to measure the phase (φ) and modulation (m) of the emission, independent of the phase shift and demodulated due to multiple scattering events.

When a fluorescent-sample is illuminated with intensity-modulated light, the emission is delayed in phase by an angle ($\phi_\omega$) due to the lifetime (τ) of the excited state. The emission is also demodulated by a factor $m_\omega$ relative to the modulation of the incident light. For a single exponential decay the phase and modulation are related to the decay time τ by $$m_\omega = (1+\omega^2\tau^2)^{-\frac{1}{2}} \tag{6}$$

here ω is the light modulation frequency in radians/sec. If the fluorescence decay is a single exponential then the same lifetime is recovered independently of light modulation frequency; where ω=2π×frequency (in Hz), and $$N_\omega J = \sum_i \frac{\alpha_i \omega \tau_i^2}{(1+\omega^2\tau_i^2)}$$

$$D_\omega J = \sum_i \frac{\alpha_i \tau_i}{(1+\omega^2\tau_i^2)}, \tag{7}$$

and $$J = \sum_i \alpha_i \tau_i \tag{8}$$

When the light pulse enters the scattering media it is time delayed ($t_L$) due to multiple scattering events. The magnitude of the time-delay $t_L$ is expected to increase with increasing depth in the sample. Additionally, the pulse is broadened due to multiple path lengths, which is most evident on the rising side of the pulse. This effect is analogous to a transit time spread in a photomultiplier tube (PMT), and hence we refer to this time as Δt. And finally the light decays due to sample absorption and/or migration away from the detector. We refer to the decay time as $t_D$, not to be confused with a fluorescence decay time (τ or $\tau_i$).

For the phenomenological model the phase angle of the re-emergent light, without interacting with any fluorophore, is given by $$\phi_\omega = \arctan(\omega t_D) + \omega t_L. \tag{9}$$

The phase angle due to the time delay ($t_L$) is given by $\Phi_L = \omega t_L$, and is therefore strongly dependent on the light modulation frequency ω (radians/sec). The decay time $t_D$ behaves analogously to the fluorescence lifetime (Eq. 9). The modulation of the re-emergent scattered light is given by $$m_\omega = m_{\Delta t} m_D, \tag{10}$$

where $$m_{\Delta t} = (1+\omega^2\Delta t^2)^{-\frac{1}{2}}, \tag{11}$$

$$m_D = (1+\omega^2 t_D^2)^{-\frac{1}{2}}, \tag{12}$$

Equation (10) is analogous to the usual relationship between a decay time and demodulation. We note that the modulation values are not sensitive to the phase of the scattered light, and hence not sensitive to $t_L$, since $t_L$ does not appear in Equations (11)–(12). This model was found to account for the frequency-domain data, so the parameters $t_D$, $t_L$ and Δt are adequate to describe the re-emerged scattered light.

The fluorophore is excited by the migrating light pulse but the "excitation pulse" is not the original δ-function, but rather the time-delayed and broadened pulse. Measurements of the emission, relative to the pulse which arrives at the sensor, will provide the correct decay time of the sensor. However, because there is no wavelength change with scattering, it is not experimentally possible to select the light which has been scattered from the same position as the sensor. The detected scattered light will be dominantly due to scattering from the surface of the solution or skin. In contrast, the fluorescence will be excited with the delayed and broadened pulse which has migrated down to the sensor, and the emission will be delayed and broadened as it migrates to the surface. Consequently, the phase and modulation values ($\phi_\omega^S$ and $m_\omega^S$), measured relative to light scattered from the surface(s), will contain contributions from both time-dependent photon migration and the lifetime of the fluorophore. For a single exponential lifetime ($\tau$) these values will be $$\phi_\omega^S = \arctan(\omega\tau) + \arctan(\omega t_D) + \omega t_L \quad (13)$$

$$m_\omega^S = (1+\omega^2\tau^2)^{1/2}(1+\omega^2 t_D^2)^{-1/2} m_{\Delta t}. \quad (14)$$

Equations (13) and (14) will strictly correct for measurement of the emission relative to the excitation pulse, as could be observed with a mirror in front of the fibers in place of the scattering solution.

Examination of Equations (13) and (14) reveal that the effects of $\tau$ or $t_D$ are mathematically similar, so that it is not possible to recover both values ($\tau$ and $t_D$) from measurement of the emission relative to the light scattered from the surface. The time delay $t_L$ appears in a linear manner, and does not contribute to the modulation, so this value can be found from the frequency-domain data. Fortunately, the values of the decay time $t_D$ are modest for all but the shortest lifetimes. For instance, the value of $t_D$ for a position 4 mm deep in the 1% intralipid in only 140 ps. Hence, for lifetimes 1 ns and longer use of the values of $\phi_\omega^S$ and $m_\omega^S$ provide a good approximation ($T_{app}$) to the true lifetime ($\tau$)

$$\phi_\omega^S = \arctan(\omega\tau_{app}) + \omega t_L \quad (15)$$

$$m_\omega^S = (1+\omega^2\tau_{app}^2)^{-1/2} m_{\Delta t}. \quad (16)$$

In practice the values of $t_L$ and $\Delta t$ are determined from the frequency-domain data ($\phi_\omega^S$ and $m_\omega^S$) because of their distinct contribution in Equations (15) and (16). In particular, we found that the use of $\tau_{app}$ from Equations (15) and (16) was adequate to recover a single exponential decay.

As described above, the scattered light is dominated by light scattered from near the surface, whereas the fluorescence originates from the embedded sensor deeper in the sample. Consequently, the value of $\phi_\omega^S$ and $m_\omega^S$ contains contributions from $t_m$, $t_L$ and $\Delta t$ (Eqs. 15 and 16). This difficulty can be avoided using a reference fluorophore of known lifetime at the same location as the sensor. In this way, we can use an emission filter to separate the emission of the reference from the scattered light.

In the present experiments we replaced the sensor with a reference fluorophore emitting at the same wavelength as the sensor. Alternatively, one could use adjacent sensors and reference fluorophores which emit at different wavelengths, and isolate the desired emission with optical filters. The use of a reference fluorophore corrects for the effects of light scatter while the excitation is traveling to the sensor, and the emission is migrating to the surface. In both cases the effects of scattering are the same, and the only difference in the re-emergent light is due to the different lifetime of the sample and reference fluorophore. In the present analysis we are ignoring the effects of wavelength, which are expected to be minor for the small wavelength difference between the scattering and emission wavelengths.

The use of a reference fluorophore requires correction for its decay time. Suppose the reference displays a single exponential decay $\tau_R$. The measured phase angle of the sensor, relative to the reference fluorophore, is smaller than the true value due to the phase of the reference fluorophore ($\phi_R$). Similarly, the modulation of the sensor, measured relative to the reference, is larger than the true value due to the decreased modulation of the emission of the reference compared to the modulation of the excitation. The actual phase ($\phi_\omega$) and modulation ($m_\omega$) values can be calculated from the observed values relative to the reference fluorophore using $$\phi_\omega = \phi_\omega^{obs} + \phi_R \quad (17)$$

$$m_\omega = m_\omega^{obs}(1+\omega^2\tau_R^2)^{-1/2} \quad (18)$$

where $\tan \phi_R = \omega\tau_R$. In this case, the measured phase and modulation values are corrected for the effects of time-dependent photon migration, and if desired, can be used to recover a multi-exponential decay.

Figure 4:
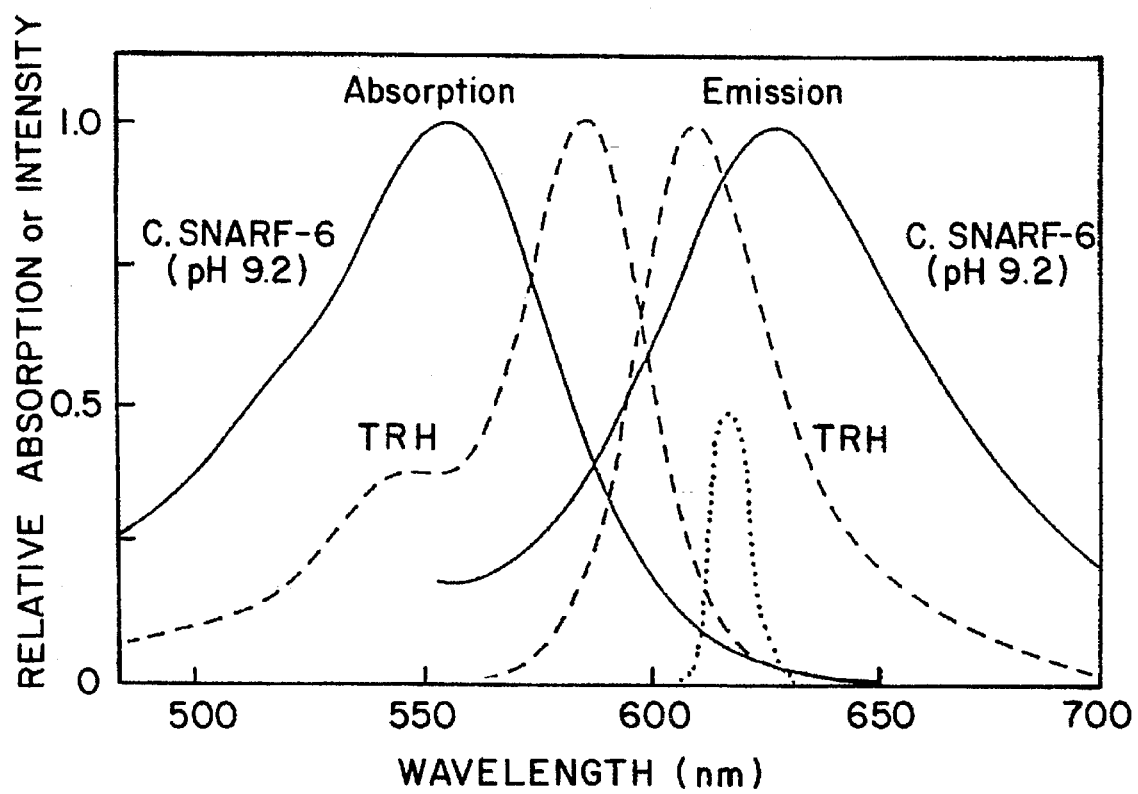
FIG. 4 Absorption and emission spectra of the pH sensor Carboxy SNARF-6 (CF6) and the reference fluorophore Texas Red Hydrazide (TRH). Also shown (. . . . .) is the transmission profile of the 620 nm interference filter used to isolate the emission. Intralipid was not present.

We examined the effects of a scattering media on the frequency-domain measurements, using fluorophores contained in microcuvettes located below the surface of the intralipid (FIG. 2). By placing the fluorophores within the microcuvette, we avoided changes in the lifetime due to possible molecular interactions of the fluorophore with the intralipid. Two fluorophores were selected for these experiments: Texas Red Hydrazide (TRH) and Carboxy SNARF-6 (CS6). Absorption and emission spectra of these fluorophores are shown in FIG. 4. Both fluorophores can be excited with the 570 nm cavity-dumped output of our R6G dye laser, or by the mode-locked output of the Argon-ion laser at 514 nm. CS6 was selected as a pH indicator whose mean lifetime depends on pH. TRH was chosen because its emission could be observed at the same wavelengths as used for CS6. The intensity decay TRH in the absence of intralipid is essentially a single exponential, and there are no significant effects of pH on its lifetime.

Figure 5:
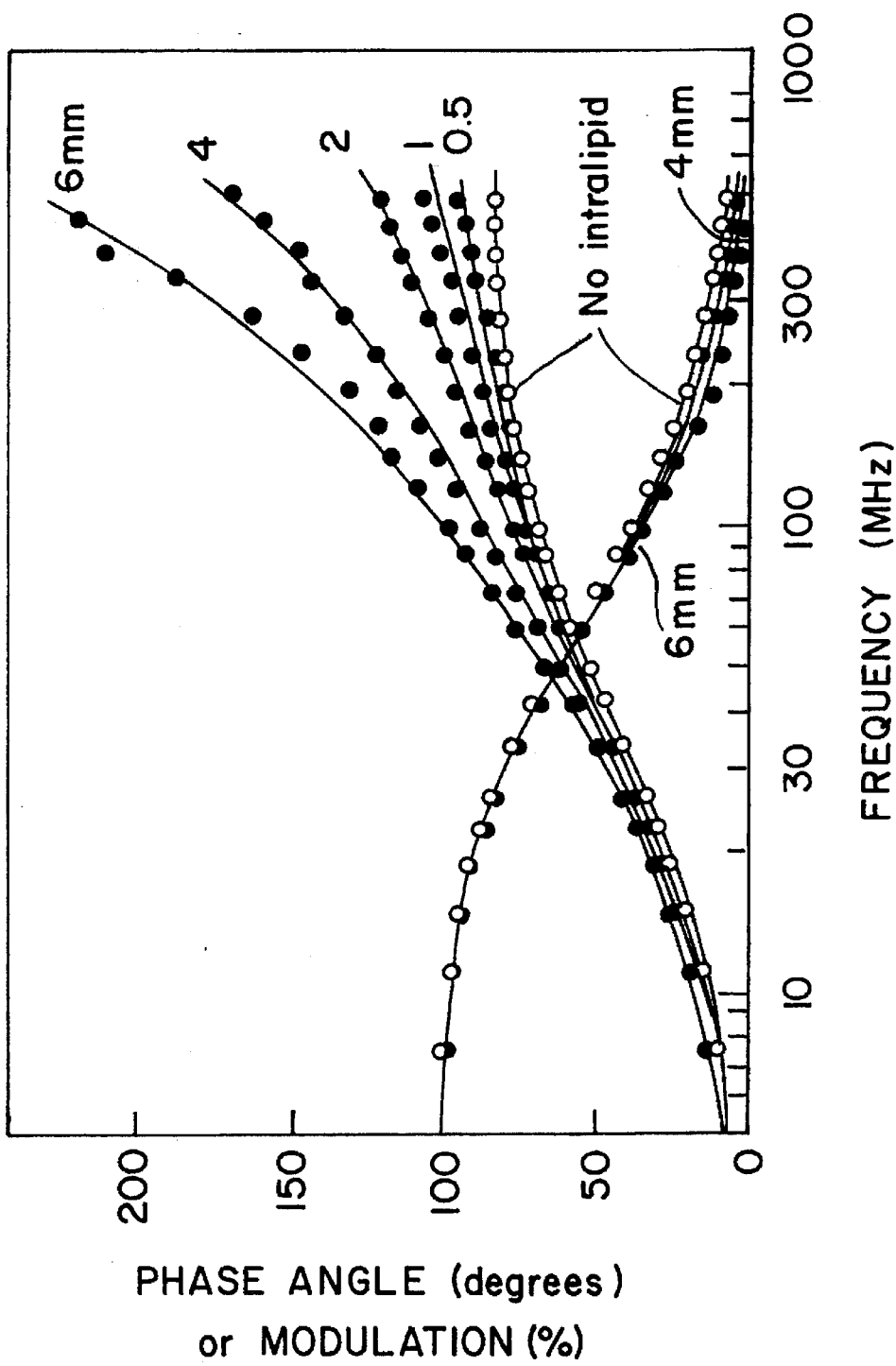
FIG. 5 Frequency-response of TRH in the microcuvette at various depths below the intralipid surface.

Frequency-domain intensity decay data of TRH are shown in FIG. 5. These data were obtained for TRH in the microcuvette, located at various depths below the intralipid surface. The phase and modulation values were measured in the usual manner, by comparing the phase and modulation of the emission at 620 nm with the phase and modulation of the scattered light at the excitation wavelength of 570 nm. In the absence of intralipid the phase values show the usual dependence on light modulation frequency; at high light modulation frequencies the phase angle approaches 90°, and the modulation decreases toward zero. In the presence of intralipid, the phase angles exceed 90°, which cannot be explained by decay of directly excited species. Phase angles in excess of 90° can result only from excited state reactions or time delays in the detected signal due to some process such as time-dependent photon migration, different path lengths for scattered and fluorescent light, or color effects in the detector. In the present case the rapidly increasing phase angles are due to the effects of the delay time $t_L$, which results in increasing large phase angles at higher light modulations frequencies (Eqs. 13 and 17). It is apparent that the effects of $t_L$ on the phase angles prevents direct use of the phase angle for determining the lifetime. In contrast, $t_L$ does not affect the modulation, and the effects of $\Delta t$ are modest. Consequently, the modulation values, measured relative to the surface scatter, can provide a reasonable estimate of the lifetime of the embedded probe.

The data in FIG. 5 shows the apparent decay time was taken as representative of the decay time of TRH (Table I). We also examined the frequency-domain data for CS6 at pH 9.2 when the intensity decay is dominated by a component with $\tau$=1.15 ns. As the depth of the microcuvette is increased, the delay time increases, as does the transit time spread. The values of the delay time increase approximately linearly with depth, and are consistent with a mean path length about 10- to 15-fold larger than the time-of-flight for the geometric distance between the surface of the intralipid (excitation source), the position of the microcuvette, and surface of the intralipid back (emission collection). The transit time spread also increases with depth, which suggests that the emission is affected by broadening of the pulse prior to its arrival at the sample, and again during migration of the fluorescence to the surface.

The decay times ($\tau$) recovered for TRH and CS6 are close to the expected values of 4.1 and 1.15 ns, respectively for all depths of the microcuvette in the intralipid (Table I).

TABLE I

Intensity decays of Texas Red Hydrazide (TRH) and Carboxy SNARF-6 (CS6) in capillary tubes at various depths in the intralipid suspension[a].

| Depth (mm) | Dye | $\tau_{app}$ (ns) | $t_L$ (ps) | $\Delta t$ (ps) | $\chi_R^2$ |
|---|---|---|---|---|---|
| No intralipid | CS6 | 1.09 | −18 | <0> | 1.3 |
|  | TRH | 4.10 | −34 ± 2 | 67 ± 83 | 1.5 |
| 0.5 | TRH | 3.84 | 59 | 157 ± 36 | 1.9 |
| 1.0 | TRH | 3.94 | 132 | 156 ± 35 | 1.7 |
| 2.0 | CS6 | 1.22 | 208 | 190 ± 10 | 1.0 |
|  | TRH | 3.99 | 226 | 205 ± 66 | 8.2 |
| 4.0 | CS6 | 1.33 | 473 | 350 ± 32 | 15.0 |
|  | TRH | 4.20 | 480 | 376 ± 86 | 18.0 |
| 6.0 | TRH | 3.89 | 847 | 957 ± 170 | 65.9 |

[a]1.0% intralipid suspension, 20° C., excitation at 570 nm, emission at 620 nm. The Carboxy SNARF-6 was in 80 mM tris, pH 9.2.

Also, the FD data appears to be adequately fit by a single exponential decay, as can be seen from the reasonable values of $\chi_R^2$ from 1 to 2. The elevated values of $\chi_R^2$ for sensors 4 and 6 mm deep in the intralipid appears to be the result of a decreased signal-to-noise ratio for the weaker signal. The values of $\chi_R^2$ were not improved by using a multi-exponential decay time. These results suggest that for lifetimes longer than 1 ns, the effects of time-dependent photon migration did not significantly alter the apparent decay times ($\tau_{app}$) relative to the time values.

Figure 6:
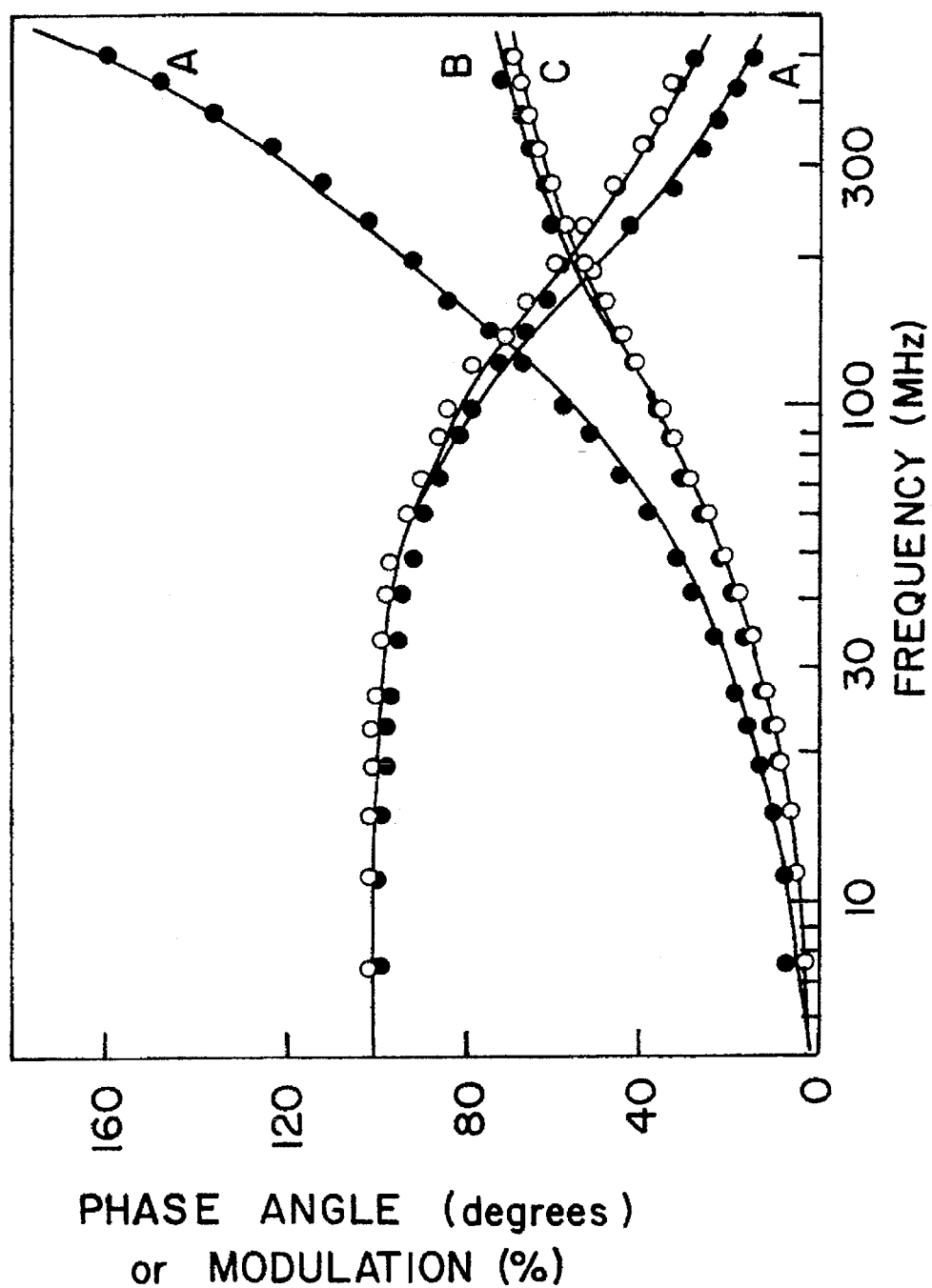
FIG. 6 Frequency-response of CS6, in the microcuvette 4 mm below the intralipid surface, when measured relative to the scattered light (A), relative to the TRH standard (B), and without intralipid (C).

Lifetime measurements can be obtained by using a reference fluorophore at the same location as the sensor. These measurements are shown in FIG. 6 where the sensing fluorophore is CS6 and the reference fluorophore is TRH. For these measurements, the CS6 and the TRH reference were contained in the microcuvettes. When measured relative to the surface scattered light, the phase angles and modulations show the usual effects of the time delay and transit time spread (FIG. 6). When measured relative to TRH, the phase angles (B) and modulations are essentially identical to that found in the absence of intralipid (C). These results illustrate how the use of a reference fluorophore corrects for the effects of time-dependent photon migration.

TABLE II

Intensity decays of Carboxy SNARF-6 (pH 9.2) measured relative to the excitation source and to the fluorescent reference TRH[a].

| Scattering Condition | $\tau$ or $\tau_{app}$ (ns) | $t_L$ (ps) | $\Delta t$ (ps) | $\chi_R^2$ |
|---|---|---|---|---|
| Relative to the excitation source |  |  |  |  |
| $\tau_{app}$ (ns) |  |  |  |  |
| No intralipid | 1.09 | −18 | ~0 | 1.3 |
| In intralipid,[b] 2 mm | 1.22 | 208 | 190 | 1.0 |
| In intralipid, 4 mm | 1.33 | 473 | 351 | 15.0 |
| Relative to the fluorescent reference TRH |  |  |  |  |
| $\tau$ (ns) |  |  |  |  |
| No intralipid | 1.17 | −33 | ~0 | 1.2 |
| In intralipid, 2 mm | 1.14 | −46 | ~0 | 2.7 |
| In intralipid, 4 mm | 1.18 | −22 | ~0 | 7.0 |

[a]Excitation at 570 mm, emission at 620 nm, 20° C. 1.0% intralipid suspension. The Carboxy SNARF-6 was in 80 mM tris, pH 9.2.
[b]Depth under surface of intralipid suspension.

Additional data and analyses using the reference fluorophore are shown in Table II. When measured relative to surface scatter, the analysis using Equations (20) and (21) shows that significant values of $t_L$ and $\Delta t$ are required to account for the data. When measured relative to TRH (Eqs. 22 and 23), the values of $t_L$ and $\Delta t$ are near zero, indicating that it is no longer necessary to consider these effects when using a reference fluorophore.

To further illustrate the usefulness of the reference fluorophore a multi-exponential analysis of the intensity decay of CS6 using Equations (5)–(9) was performed. In the absence of intralipid, the intensity decay is a double exponential (Table III), as can be seen from the 10-fold decrease in $\chi_R^2$ from 6.7 to 0.6 for the two exponential fit.

TABLE III

Multiexponential intensity decay analysis of Carboxy SNARF-6 (pH 9.2) measured relative to its excitation source and to the fluorescent reference TRH.

| Reference/Sample | $\tau_i$ (ns) | $\alpha_i$ | $f_i$[a] | $\chi_R^2$ |
|---|---|---|---|---|
| Surface scatter/ | 1.06 | 1 | 1 | 6.7 |
| CS6 without intralipid | 0.46 | 0.188 | 0.084 |  |
|  | 1.15 | 0.812 | 0.916 | 0.6 |
| TRH/ | 1.10 | 1 | 1 | 20.9 |
| CS6 without intralipid | 0.16 | 0.243 | 0.040 |  |
|  | 1.19 | 0.757 | 0.960 | 0.9 |
| TRH/ | 1.03 | 1 | 1 | 38.7 |
| CS6 under 2 mm of | 0.17 | 0.310 | 0.062 |  |
| intralipid | 1.16 | 0.690 | 0.938 | 1.6 |
| TRH/ | 1.12 | 1 | 1 | 10.4 |
| CS6 under 4 mm of | 0.30 | 0.128 | 0.036 |  |
| intralipid | 1.18 | 0.872 | 0.964 | 5.0 |

[a]The fractional contribution of each component to the steady-state intensity can be calculated using $f_i = \alpha_i \tau_i / \Sigma_j \alpha_j \tau_j$.

However, the amplitude of the shorter 0.16 to 0.46 ns component is weak and contributes only 4 to 8% of the total intensity. In spite of this weak contribution, two decay times and amplitudes of CS6 were recovered from 2 and 4 mm of intralipid when measured using the reference fluorophore. This result suggests that even complex intensity decays can be quantitatively recovered from sensors embedded in highly scattering media.

To avoid confusion, we note that double-exponential intensity decays of CS6 were not recovered when using Equations (16) and (17) (Table II).

In this case there is a weak contribution of the short-lived component, and it appears that the value of $t_L$ can vary and to some extent account for the short-lived component in the decay of CS6. For instance, in the absence of intralipid (Table II), the value of $t_L=18$ ps may be a consequence of the multi-exponential decay of CS6. An advantage of using the reference fluorophore is that the data can be analyzed using Equations (5)–(9), without the use of $t_L$ and $\Delta t$ as additional parameters.

Experiment II

Figure 7:
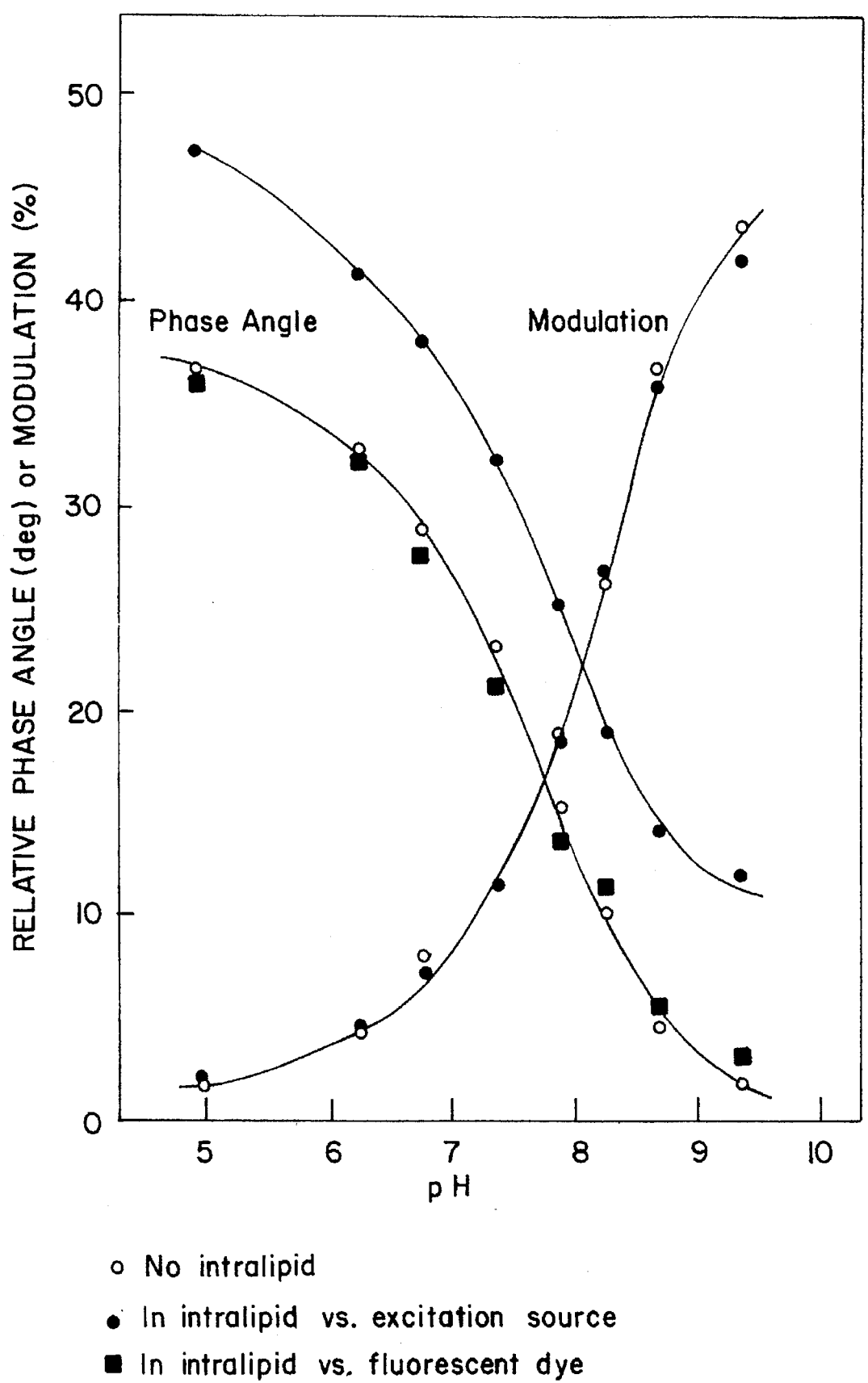
FIG. 7 pH sensing at a 4 mm depth in 0.25% intralipid using CS6. Excitation was the mode-locked output of an Argon-ion laser at 514 nm. The emission was detected at 640 nm. Phase and modulation data were obtained without intralipid (o), in intralipid versus the scattered light from the surface (●) and in intralipid versus the TRH standard (■).

To illustrate the possibility of non-invasive pH measurements, we examined a series of CS6 solutions of various pH. The experimental conditions were changed to 514 nm excitation and 640 nm emission, which selects for excitation of the acid form and detection of the base form of CS6, and results in an apparent $pK_a$ value near 7.5 as seen from the phase angle and 8 for the modulation. The calibration curve for these experimental conditions is shown in FIG. 7. When measured relative to surface scatter, the phase angles (●) are larger than the true values and do not reveal the correct pH. When measured relative to the TRH standard, the correct phase angles are observed (■) demonstrating the possibility of non-invasive pH sensing in scattering media. It is interesting to notice that for CS6 under these experimental conditions, essentially the same modulation values are measured versus surface scatter (●) as measured without intralipid (o).

Experiment III

Figure 8:
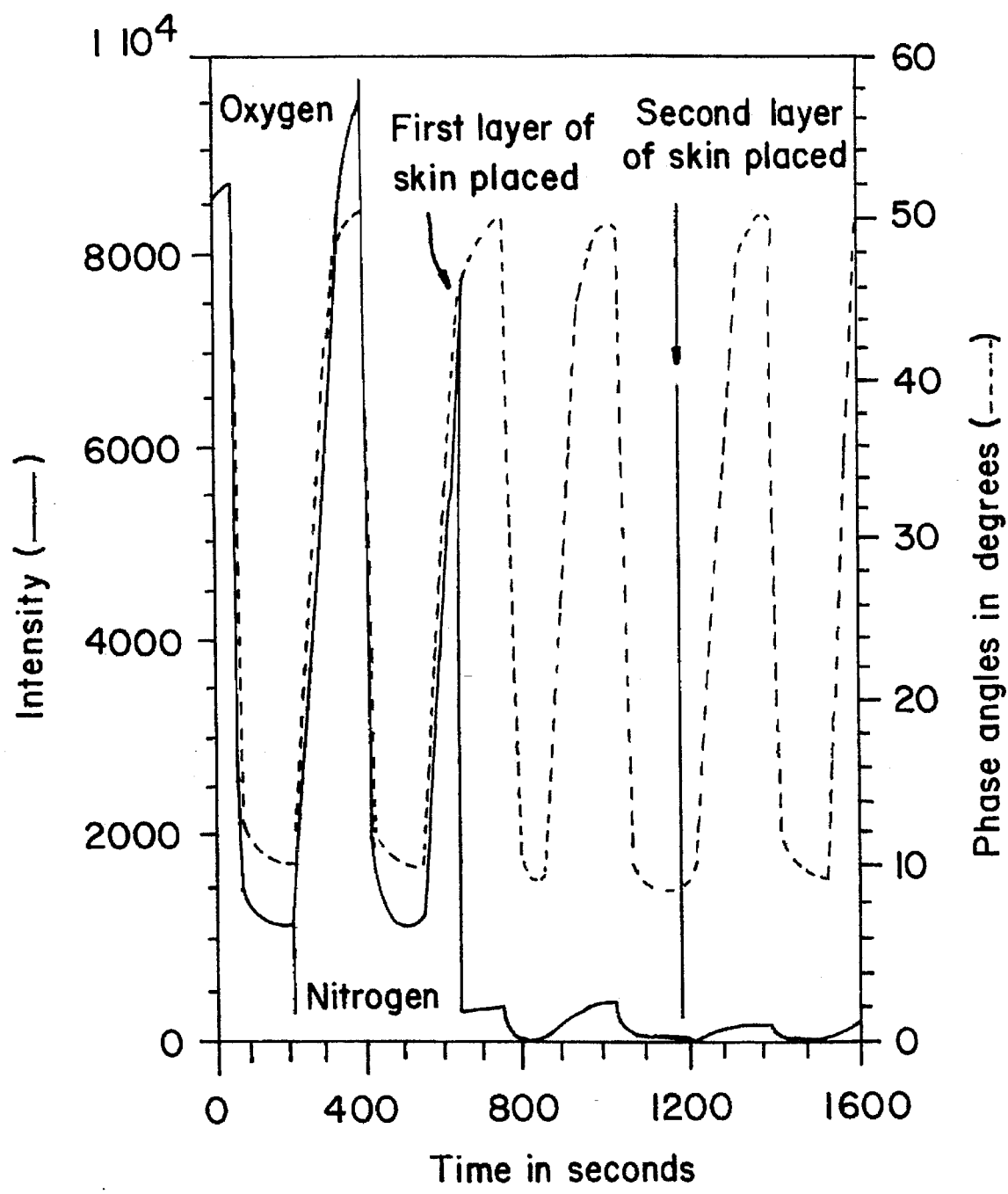
FIG. 8 shows the change in phase angle differences of fluorescent emissions from various excitation intensities measured through layers of chicken skin.

To demonstrate transcutaneous sensing, experiments were conducted using layers of chicken skin to block both excitation and emission light paths during spectra acquisition. Chicken skin is optically similar to human skin. FIG. 8 shows real time fluorescence intensity and phase angle measurements (at 750 KHz) as oxygen and nitrogen were alternately bubbled through the fluorophore solution. The measurements were made first with no skin, one layer of skin and finally with two layers of skin in both the excitation and emission paths. While a 50 fold decrease in the intensity response occurred, the phase angle measurements were unaffected by the presence of the skin. This demonstrates the independence of phase angle measurements to changes in skin thickness and attenuation in excitation light intensity. Provided a minimum measurable emission is available (the quantity of light required for measurement at a tolerable signal to noise level, is governed entirely by the photodector) the phase angles are independent of the attenuating effects that limit fluorescence intensity based measurements.

The results described above demonstrate that lifetime-based sensing is possible for sensors imbedded in turbid media. The measurements were performed using a mode-locked Argon-ion laser and a ps dye laser light source. Based on these results it would be apparent for one skilled in the art to adapt simple instrumentation for use in the doctor's office, at home, or even as portable devices.

Medical phase-modulation fluorometers can be constructed using currently available probe and electro-optics technology. Such a device is shown in FIG. 1, which illustrates one possible configuration for non-invasive measurements. The sensing patch may be implanted under the skin, and of course, would be permeable to the analyte of interest. The lifetime of the sensing patch could be measured using the methods described in this report. There has been rapid development of long-wavelength fluorophores, many of which can be excited with currently available laser diodes. It is well known that the optical output of laser diodes can be intensity modulated to GHz frequencies, and that wavelengths above 620 nm readily penetrate the skin, so that laser diodes can be the light source for imbedded phase-modulated sensors. Laser diodes have already been used for frequency-domain (FD) lifetime measurements, for FD lifetime measurements through fibers, and for a fiber-optic pH sensor. New classes of fluorescence sensors are emerging, which display long decay times over 100 ns, and that such long-lived fluorophores can be excited with simple modulated light sources such as an electroluminescent device. It has even been possible to develop a sterilizable sensor using these long-lived fluorophores. For these longer lifetimes, the effect of time-dependent photon migration will be less significant, and can possibly be neglected. Lifetime-based sensing in tissues is clinically practical with currently available technology.

Advances in the chemistry of molecular recognition allow tailored recognition of analytes, thus providing a whole new class of biochemically significant substances that can be instantaneously and non-invasively monitored. Among the representative blood components that can be measured include blood gas levels, metal content, anion and cation levels, hormones, fats, and carbohydrates. Elements suitable for monitoring in this manner are $pO_2$, pH, $pCO_2$, $Na^+$, $K^+$, $Ca^{2+}$, $Mg^{2+}$, $PO^{2-}$, Estrogen, Progesterone, Thyroxine, IL-1, high and low density cholesterol, glucose levels and mixtures thereof. These emerging applications of fluorescence can be seen by the growth and introduction of improved methods for immunoassays, enzyme-linked immunoassays (ELISA), protein and DNA staining, and protein and DNA sequencing.

Other objects, features and advantages of the present invention will become apparent to those skilled in the art from the following detailed description and attached drawings. For simplicity and clarity, a limited number of preferred embodiments of the present invention are described, but it is understood that it is not to be construed as limiting the invention thereto, but rather it should be viewed as representative embodiments of the broader inventive concept.

One preferred embodiment of the invention pertains to glucose detection as a means for controlling diabetes which is discussed in detail below.

while the acute problems of diabetes can be controlled, diabetics suffer a number of long-term adverse health effects which result from inadequate control of blood glucose. The health problems include blindness and cardiovascular diseases, which appear to be a consequence of the accumulation of glycosylated proteins and their metabolic products. Amelioration of these long term effects seems possible if blood glucose can be controlled within normal physiological limits. Unfortunately, such control is not available, in part due to our present inability to continuously monitor blood glucose. Present methods to measure blood glucose require a sample of fresh blood, which is painful and inconvenient, so that patients perform the least frequent testing possible and thus suffer extreme fluctuations in glucose levels.

Non-invasive measurement of blood or tissue glucose would be a significant advance for diabetics. Tissue glucose closely follows blood glucose, with about a 10 minute time lag, so that a sensor for subdermal tissue glucose can be expected to provide adequate information for controlling glucose levels. Many attempts have been made to develop a method for non-invasive glucose sensing, including transdermal NIR spectroscopy the measurement of glucose in the eye by optical rotation, or transducing the glucose concentration to changes in pH, or oxygen concentration. However, the lack of a commercially available alternative to (invasive) blood sample based enzymatic glucose analyzers suggests that all these approaches are yet to materialize as practical, low-cost devices.

An advantage of phase-modulation fluorometry for sensing is the use of cross-correlation detection, which results in an increased signal-to-noise ratio and rejection of undesired harmonics. The gain of the photo-multiplier tube (PMT) detector is modulated by a small voltage applied to one of its dynodes. The gain modulation frequency is offset from the light modulation frequency by a small amount, typically 25 or 40 Hz. The phase and modulation information are preserved in the low frequency signal, and $\theta_\omega$ and $m_\omega$ then easily measured with simple electronics. The AC component of the signal is typically passed through a 1 Hz wide filter, which rejects undesired harmonics. Cross-correlation electronics or numerical filtering results in phase and modulation measurements which are correct irrespective of the form of the light and gain modulation. The measurements may be made with either sinusoidal or pulse source modulation. The frequency synthesizers for a sensing application require that the two frequencies (f and f+$\Delta$f) be phase-locked.

Figure 9:
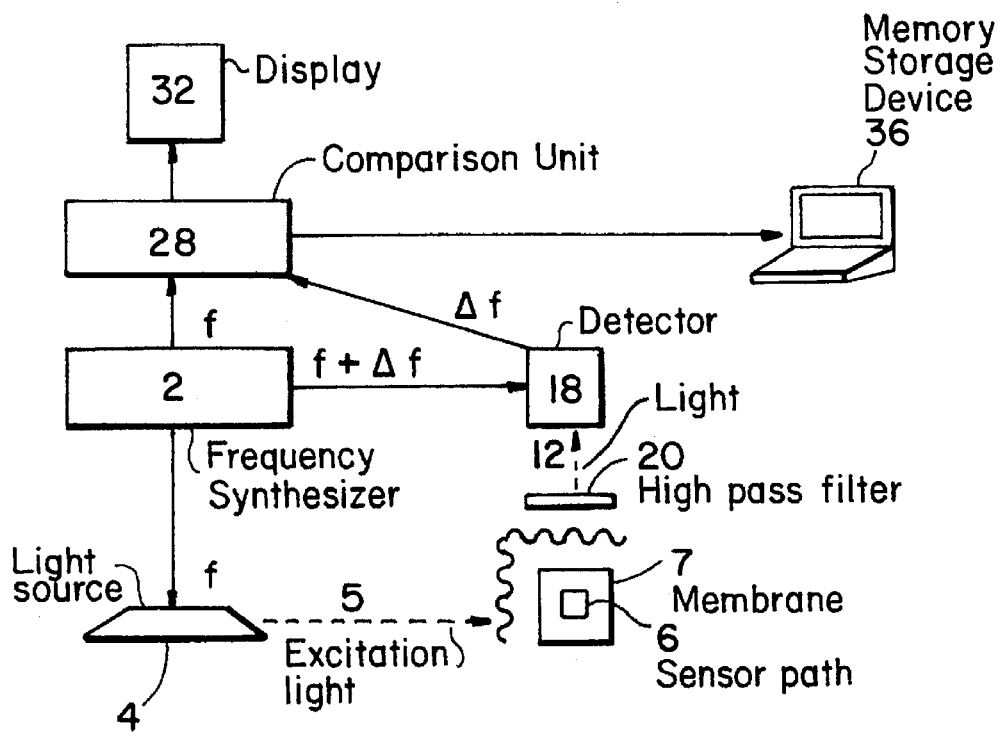
FIG. 9 is a block diagram of a representative system for trans-cutaneous analyte monitor.

FIG. 9 depicts an example of a flow scheme for using the apparatus of this invention. Frequency synthesizer 2 transmits an excitation frequency to light emitting source 4. The light emitting source 4, such as a laser diode (i.e. Toshiba model TOLD9520) emits excitation light 5 with a −3 db bandwidth of 0.07 to 1.7 MHz in concert with the frequency of frequency synthesizer 2. Subcutaneous sensor patch 6 is implanted in a patient's arm, or other readily accessible portion of the body. Multiple patches may be implanted if required for diagnostic reasons, or a single sensor patch 6 capable of detecting multiple biologically significant substances can be used.

Figure 12:
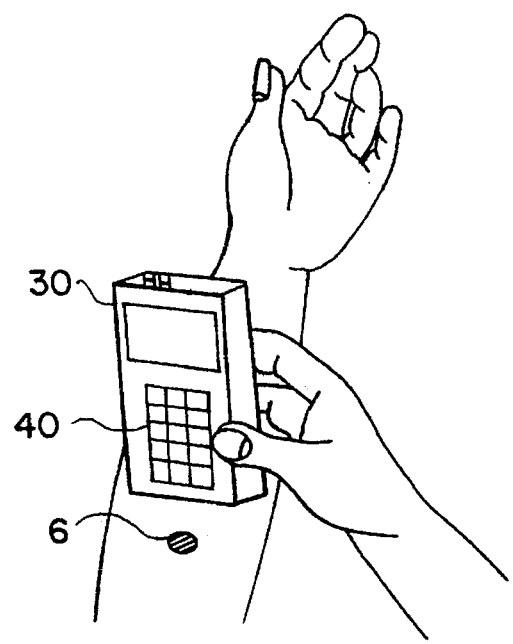
FIG. 12 is a view of a portable trans-cutaneous analyte monitor with a display and keyboard.

Sensor patch 6 is a permeable subcutaneous biocompatible implantable element containing a fluorescent donor labelled glucose binding protein and a fluorescent acceptor labelled sugar. The sensor may be of a planar or cylindrical shape with a membrane 7 permeable to the relevant substance. In this embodiment, cellulosic dialysis membranes are used. The process of fluorescent emission is discussed in greater detail below with reference to FIGS. 9 and 10. The acceptor fluorescent emission is detected by detector 18. High pass filter 20 may be incorporated before detector 18 to reduce noise. Detector 18 is comprised of one or more photomultiplier tubes 22 for collection of emitted light 12 from sensor patch 6. Detector 18 may be enclosed in a portable housing 30 (as shown in FIG. 12) which allows light entry through an aperture (not shown).

The received emission light 12 wavelength and temporal characteristics is compared to the signal generated by frequency synthesizer 2 in comparison unit 28, wherein an algorithm correlates the wavelength and temporal characteristics of the change in emission light 12 from excitation light 5 to quantify the amount of biologically significant substances present. The algorithm is computed from empirical data for the various biologically significant substances, and the process of developing a mathematical model of natural phenomena is well known to those skilled in the art.

The comparison can be performed by any integrated circuits of this type well known in the art, including the Analog Devices Model 630 IC. This preferred embodiment uses the phase shift between emitted light 12 and excitation light 5 to solve an algorithm to determine the amount of relevant substances present at sensor patch 6. Display 32 communicates the quantitative result of the comparison algorithm to the operator, and the quantity is electrically stored in memory storage device 36.

Figure 10:
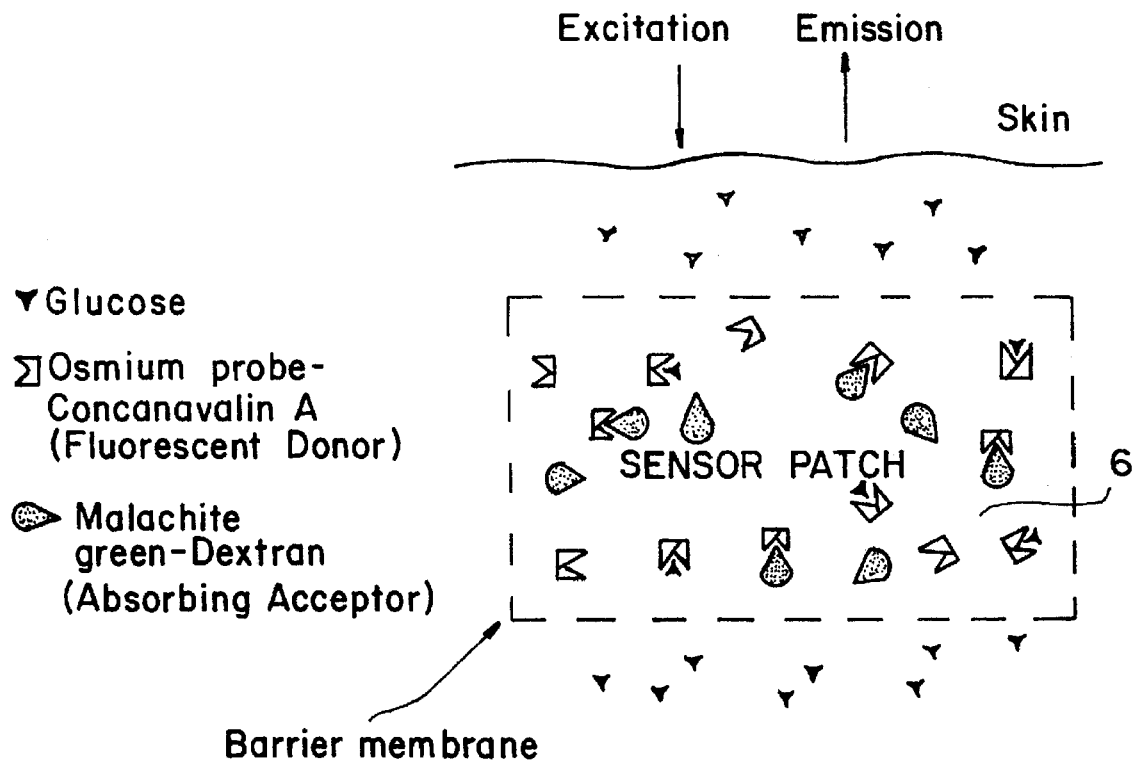
FIG. 10 is representative of the interaction between the biologically significant substance, an analyte donor and a absorbing acceptor for the detection of glucose.
Figure 11:
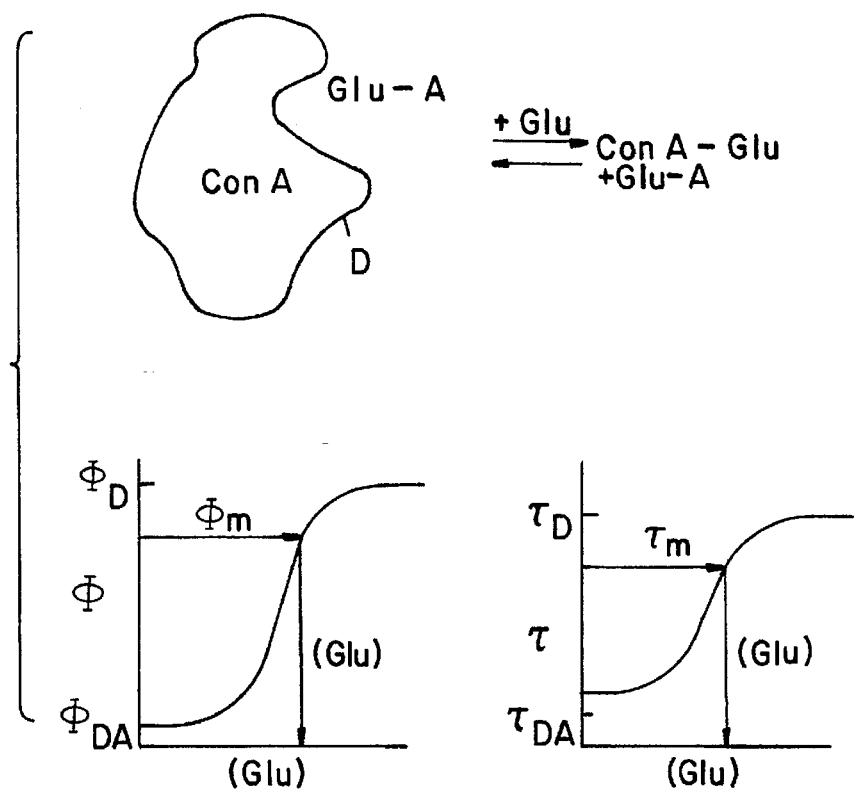
FIG. 11 is a graph displaying the phase and life time shifts that occur when glucose displaces the acceptor from the donor.

FIG. 10 depicts bio-compatible sensor patch 6. In this embodiment, donor-labeled protein Concanavalin A (ConA) is used in contact with acceptor-labeled dextran. Since both the donors and acceptors are high molecular weight species, they can be trapped behind glucose-permeable membrane 7. Endogenous glucose will bind to ConA and displace it from the dextran. Consequently, the donor lifetime will increase due to decreased proximity to the acceptor, which will be measured as an increase in phase angle, as depicted in FIG. 11.

Normally, sensor patch 6 will be subcutaneously implanted for hygiene and cosmetic reasons. However, there may be a donor-acceptor combination needed to detect a particular biochemically relevant substance for which the excitation light frequency of the donor is incapable, or only marginally capable, of skin penetration.

The inventive detection system is compatible with either digital or analog circuit design, and with fiber optic or wire electrical connections. The preferred embodiment for reliability, low cost and speed is a digital circuit using fiber optic transmission lines.

Graphical displays 32, consisting of liquid crystals, or paper printouts, are used to communicate the quantitative result of the comparison algorithm, and the data is stored in memory storage device 36, such as a semiconductor, computer or other electronic data storage device.

Keyboard 40, as shown in FIG. 12, can be added to the housing for inputting patient identification numbers, time information, or telephone numbers to identify, amplify, and transmit the data collected from the sensor patch. The data can be internally stored, or transmitted immediately via telephone, radio, microwave, infrared or equivalent means to a remote location.

The amount of storage capacity incorporated in the apparatus is design dependent. A unit used in a hospital which will be in continuous or near continuous contact with the main data storage system will require little data storage capacity. A unit designed to be used at remote sites or in field hospitals will require more internal storage capacity if there are longer periods and/or more individual patient's data inserted before each data transmission. As the costs for memory storage have declined, the addition of enough memory to retain daily readings for later transmission to a physician will not be cost prohibitive or bulky.

Another embodiment of this invention can be used to detect levels of oxygen. The clinical assessment of oxygenation in arteries and other tissues is of significant importance in monitoring critically ill patients. Arterial oxygenation problems are a common indication of loss of hemoglobin or of deteriorating lung function and indicates tissue hypoxia with resulting loss of function. In general, disturbances in oxygenation result in decreased performance from organs highly dependent on oxygen, such as the hear and brain.

An Osmium based metal-ligand complex is chosen as a donor, for example $[Os(bpy)_3]$ $I_2$ and Malachite green as the acceptor with a light emitting source 4 chosen which emits a red excitation light. An alternate embodiment contains a Ruthenium ligand complex [Ru(bpy)$_3$]Cl$_2$ as a donor with an Acceptor of reactive Blue and a doubled frequency blue excitation light. In both examples there is adequate spectral overlap between the donor emission and the acceptor absorption to expect fluorescent resonance energy transfer (FRET) to occur.

The excitation source is an inexpensive blue LED that is modulated simply by varying its supply current. The phase fluorimetric oxygen sensor measures the quenching by oxygen of the transition metal complex, tris [4,7-diphenyl-1,10-phenanthroline] ruthenium (II)$^{2+}$. This transduction scheme generally follows a first-order-type response to oxygen tension resulting in higher oxygen sensitivities at low oxygen concentrations. The fluorophore is immobilized in a membrane which has high oxygen solubility and diffusivity. The sensor is equally sensitive to gaseous and dissolved oxygen tensions. The matrix selected for gaseous analytes because of its hydrophobic nature, adding to sensor specificity. In addition, the hydrophobic matrix and the water insolubility of the ruthenium complex add to long-term sensor stability by preventing washing out and leaching of the probe.

Another preferred embodiment of this invention is a lifetime-based pH sensor. Two dyes, a high-quantum-yield fluorescence donor and a pH-sensitive acceptor whose absorbance overlaps significantly with the donor's emission are place in a hydrophilic matrix and subcutaneously implanted. Optimal energy transfer is obtained when the donor-acceptor pair are within 40-70 Å of each other. Red laser diodes (>635 nm) that permit MHz modulation are used as the light emitter source. Texas Red Hydrazide is used as the donor and Bromothymol blue as the acceptor.

Yet anther embodiment of this invention is a life-time-based CO$_2$ sensor.

In another embodiment the sensor patch may only be needed for short periods, and does not require a long indwelling device such as in post surgery recovery. Furthermore, the full implantation procedure in such situations is not cost effective or beneficial. In these cases the sensor 6 may be transcutaneously implanted microspheres or particles implanted beneath the skin by injection. The apparatus may be used to monitor patients in a hospital where each patient's information is preceded by an identifying number. The stored information is entered into a central computer file for all patients at one time, while a local record is printed for the attending physician and the data is transmitted via modem to another location for consultation.

In another embodiment a patient in a remote location can self monitor blood chemistry, or transmit the data to a physician for evaluation. This obviates the need for costly and time consuming visits to laboratories for testing and delays in waiting for the results.

In another embodiment, Emergency Medical Technicians, or military field hospital personnel, can implant the sensor patch and have quick access to various readings to aid in the diagnosis of conditions while in areas remote from analysis facilities or situations where time is critical.

In yet another preferred embodiment, multiple analyte measurement methods could be combined in one instrument, such as the combination of O$_2$, CO$_2$, and pH sensors for blood-gas monitoring.

The invention being thus described, it will be obvious that the same may be varied in many ways. Further advances will undoubtedly increase the number of biomedically significant analytes that can be measured by phase fluorometry. Such variations are not to be regarded as a departure from the spirit and scope of the invention and all such modifications are intended to be included within the scope of the following claims.

What is claimed is:

1. A trans-cutaneous analyte monitor, comprising:

a light emitting means for emitting an excitation light having predetermined wavelength and temporal characteristics;

a bio-compatible implant, said bio-compatible implant emitting fluorescence having predetermined wavelength and temporal characteristics upon absorption of said excitation light emitted from said light emitting means;

a detector means to detect said fluorescence from said bio-compatible implant, said detector means producing an electrical signal proportional to said fluorescence;

a comparison means to compare by means of lifetime-based sensing said wavelength and temporal characteristics of said light emitted from said light emitting means and said wavelength and temporal characteristics of said fluorescence from said bio-compatible implant said comparison means receiving input from said light emitting means and said detector means and having an output; and a computing means to receive said output of said comparison means and relating said comparison of said wavelength and temporal characteristics of said light emitted from said light emitting means and said wavelength and temporal characteristics of said fluorescence from said bio-compatible implant to a quantity of a selected substance present.

2. The trans-cutaneous analyte monitor of claim 1, wherein:

said predetermined wavelength and temporal characteristics of said fluorescence is altered by collisional quenching caused by the presence of a predetermined substance.

3. The trans-cutaneous analyte monitor of claim 2, wherein:

said comparison means to compare said wavelength and temporal characteristics of said light emitted from said light emitting means and said wavelength and temporal characteristics of said fluorescence from said bio-compatible implant is by means of intensity based sensing.

4. The trans-cutaneous analyte monitor of claim 1, further comprising:

a display means for displaying said quantity of said substance present.

5. The trans-cutaneous analyte monitor of claim 1, further comprising:

a memory storage device for receiving said output of said computing means.

6. A trans-cutaneous analyte monitor, comprising:

alight emitting means for emitting an excitation light having predetermined wavelength and temporal characteristics;

a bio-compatible implant, said bio-compatible implant emitting fluorescence having predetermined wavelength and temporal characteristics upon absorption of said excitation light emitted from said light emitting means, said bio-compatible implant comprises a fluorescent donor and an analyte-dependent acceptor which spectrally overlaps said fluorescent donor, said bio-compatible implant emitting fluorescence of a predetermined wavelength and temporal characteristics upon absorption of said excitation light emitted form said light emitting means, said fluorescence wavelength and temporal characteristics being altered when a predetermined substance is present;

a detector means to detect said fluorescence from said bio-compatible implant, said detector means producing an electrical signal proportional to said fluorescence;

a comparison means to compare said wavelength and temporal characteristics of said light emitted from said light emitting means and said wavelength and temporal characteristics of said fluorescence from said bio-compatible implant said comparison means receiving input from said light emitting means and said detector means and having an output; and a computing means to receive said output of said comparison means and relating said comparison of said wavelength and temporal characteristics of said light emitted from said light emitting means and said wavelength and temporal characteristics of said fluorescence from said bio-compatible implant to a quantity of a selected substance present.

7. The trans-cutaneous analyte monitor of claim 6, wherein:

said comparison means to compare said wavelength and temporal characteristics of said light emitted from said light emitting means and said wavelength and temporal characteristics of said fluorescence from said bio-compatible implant is by means of intensity based sensing.

8. The trans-cutaneous analyte monitor of claim 6, wherein:

said comparison means to compare said wavelength and temporal characteristics of said light emitted from said light emitting means and said wavelength and temporal characteristics of said fluorescence from said bio-compatible implant is by means of time domain lifetime-based sensing.

9. The trans-cutaneous analyte monitor of claim 6, wherein:

said comparison means to compare said wavelength and temporal characteristics of said light emitted from said light emitting means and said wavelength and temporal characteristics of said fluorescence from said bio-compatible implant is by means of frequency domain lifetime-based sensing.

10. A trans-cutaneous analyte monitor, comprising:

a light emitting means for emitting an excitation light having predetermined wavelength and temporal characteristics;

a bio-compatible implant, said bio-compatible implant emitting fluorescence having predetermined wavelength and temporal characteristics upon absorption of said excitation light emitted from said light emitting means, said bio-compatible implant includes an analyte-free and an analyte-bound form of a fluorescent emitter and wherein the ration of the signals at two excitation emission wavelengths is used for quantitative measurements of a predetermined substance;

a detector means to detect said fluorescence from said bio-compatible implant, said detector means producing an electrical signal proportional to said fluorescence;

a comparison means to compare said wavelength and temporal characteristics of said light emitted from said light emitting means and said wavelength and temporal characteristics of said fluorescence from said bio-compatible implant said comparison means receiving input from said light emitting means and said detector means and having an output; and a computing means to receive said output of said comparison means and relating said comparison of said wavelength and temporal characteristics of said light emitted from said light emitting means and said wavelength and temporal characteristics of said fluorescence from said bio-compatible implant to a quantity of a selected substance present.

11. The trans-cutaneous analyte monitor of claim 10, wherein:

said comparison means to compare said wavelength and temporal characteristics of said light emitted from said light emitting means and said wavelength and temporal characteristics of said fluorescence from said bio-compatible implant is by means of intensity based sensing.

12. The trans-cutaneous analyte monitor of claim 10, wherein:

said comparison means to compare said wavelength and temporal characteristics of said light emitted from said light emitting means and said wavelength and temporal characteristics of said fluorescence from said bio-compatible implant is by means of time domain lifetime-based sensing.

13. The trans-cutaneous analyte monitor of claim 10, wherein:

said comparison means to compare said wavelength and temporal characteristics of said light emitted from said light emitting means and said wavelength and temporal characteristics of said fluorescence from said bio-compatible implant is by means of frequency domain lifetime-based sensing.

14. A trans-cutaneous analyte monitor, comprising:

a light emitting means for emitting an excitation light having predetermined wavelength and temporal characteristics;

a bio-compatible implant, said bio-compatible implant emitting fluorescence having predetermined wavelength and temporal characteristics upon absorption of said excitation light emitted from said light emitting means;

a detector means to detect said fluorescence from said bio-compatible implant, said detector means producing an electrical signal proportional to said fluorescence;

a comparison means to compare said wavelength and temporal characteristics of said light emitted from said light emitting means and said wavelength and temporal characteristics of said fluorescence from said bio-compatible implant said comparison means receiving input from said light emitting means and said detector means and having an output;

a computing means to receive said output of said comparison means and relating said comparison of said wavelength and temporal characteristics of said light emitted from said light emitting means and said wavelength and temporal characteristics of said fluorescence from said bio-compatible implant to a quantity of a selected substance present;

a memory storage device for receiving said output of said computing means; and a data transfer means, said data transfer means configured to receive input from said memory storage device and whereby said quantity of said substance present stored in said memory storage device is transferred to a remote receiving station.

15. The trans-cutaneous analyte monitor of claim 14, wherein said data transfer means is a modem for data transfer to a computer.

16. The trans-cutaneous analyte monitor of claim 14, wherein said data transfer means is an antenna and transmitter to transmit said data to a receiver.

17. The trans-cutaneous analyte monitor of claim 14, wherein said data transfer means is a satellite relay.

18. A trans-cutaneous analyte monitor, comprising:
- a light source capable of emitting an excitation light having predetermined wavelength and temporal characteristics;
- a bio-compatible implant, said bio-compatible implant emitting fluorescence having predetermined wavelength and temporal characteristics upon absorption of said excitation light emitted from said light source;
- a detector means to detect said fluorescence from said bio-compatible implant, said detector means producing an electrical signal proportional to said fluorescence;
- a comparison means to compare said wavelength and temporal characteristics of said light emitted from said light source and said wavelength and temporal characteristics of said fluorescence from said bio-compatible implant by means of time domain lifetime-based sensing, said comparison means receiving input from said light source and said detector means and having an output;
- a computing means to receive said output of said comparison means and relating said comparison of said wavelength and temporal characteristics of said light emitted from said light source and said wavelength and temporal characteristics of said fluorescence from said bio-compatible implant to a quantity of a selected substance present.

19. The trans-cutaneous analyte monitor of claim 18, wherein said light source emits an excitation light in the infrared wavelength.

20. The trans-cutaneous analyte monitor of claim 20, wherein said light source emits an excitation light of a wavelength greater than about 600 nm.

21. A trans-cutaneous analyte monitor, comprising:
- a light emitting means capable of emitting an excitation light having predetermined wavelength and temporal characteristics;
- a bio-compatible implant, said bio-compatible implant emitting fluorescence having predetermined wavelength and temporal characteristics upon absorption of said excitation light emitted from said light emitting means;
- a detector means to detect said fluorescence from said bio-compatible implant, said detector means producing an electrical signal proportional to said fluorescence;
- a comparison means to compare said wavelength and temporal characteristics of said light emitted from said light emitting means and said wavelength and temporal characteristics of said fluorescence from said bio-compatible implant by means of frequency domain lifetime-based sensing, said comparison means receiving input from said light emitting means and said detector means and having an output;
- a computing means to receive said output of said comparison means and relating said comparison of said wavelength and temporal characteristics of said light emitted from said light emitting means and said wavelength and temporal characteristics of said fluorescence from said bio-compatible implant to a quantity of a selected analyte present.

22. A trans-cutaneous analyte monitor, comprising:
- a light emitting means for emitting an excitation light having predetermined wavelength and temporal characteristics;
- a bio-compatible implant, said bio-compatible implant emitting fluorescence having predetermined wavelength and temporal characteristics upon absorption of said excitation light emitted from said light emitting means;
- a detector means to detect said fluorescence from said bio-compatible implant wherein said detector measures the wavelength and temporal characteristics of said bio-compatible skin implant fluorescence, and further wherein said detector emits an electrical signal which is proportional to the fluorescence wavelength and temporal characteristics received;
- a comparison means to compare said wavelength and temporal characteristics of said light emitted from said light emitting means and said wavelength and temporal characteristics of said fluorescence from said bio-compatible implant;
- a computing means to relate said comparison of said wavelength and temporal characteristics of said intensity modulated light emitted from said light emitting means and said wavelength and temporal characteristics of said fluorescence from said bio-compatible to a quantity of a biologically significant substance present;
- a display means for displaying said quantity of biologically significant substances;
- a memory storage device for receiving said output of said computing means; and
- a data transfer means, said data transfer means receiving input from said memory storage device and whereby said quantity of said biologically significant substance present stored in said memory storage device.

23. The trans-cutaneous analyte monitor of claim 22, further comprising:
- a frequency synthesizer, wherein said frequency synthesizer products a modulated electrical output;
- wherein said light emitting means receives said modulated electrical output of said frequency synthesizer causing said light emitting means to emit an intensity modulated excitation light of predetermined wavelength and temporal characteristics;
- wherein said detector measures the wavelength and temporal characteristics of said bio-compatible implant fluorescence, and further wherein said detector emits an electrical signal which is directly proportional to the fluorescence wavelength and temporal characteristics received;
- wherein said comparison means compares the phase angle difference between said excitation light predetermined wavelength and temporal characteristics and said wavelength and temporal characteristics of said fluorescence of said bio-compatible implant; and
- wherein said computing means computes the quantity of said biologically significant substance present from said comparison of said light emitted form said light emitting means and said wavelength and temporal characteristics of said fluorescence from said bio-compatible implant.

24. The trans-cutaneous analyte monitor of claim 23, wherein:

said light emitting means is a light emitting diode.

25. The trans-cutaneous analyte monitor of claim 23, wherein:

said light emitting means is a laser diode.

26. A method to trans-cutaneously monitor analytes, comprising:

emitting a modulated excitation light from a light emitting means, said excitation light having predetermined wavelength and temporal characteristics;

implanting a bio-compatible implant, said implant emitting fluorescence having predetermined wavelength and temporal characteristics upon absorption of said excitation light emitted from said light emitting means;

detecting said fluorescence wavelength and temporal characteristics from said bio-compatible implant;

comparing said wavelength and temporal characteristics of said excitation light emitted from said light emitting means and said wavelength and temporal characteristics of said fluorescence from said bio-compatible implant; and computing said wavelength and temporal characteristics of said light emitted from said light emitting means and said wavelength and temporal characteristics of said fluorescence form said bio-compatible implant to quantify an amount of an analyte.

27. The method to trans-cutaneously monitor analytes of claim 26, comprising:

displaying said quantity of said analyte.

28. The method to trans-cutaneously monitor analytes of claim 27, further comprising:

storing in a memory storage device said output of said computing means.

29. The method to trans-cutaneously monitor analytes of claim 28, further comprising:

transferring said data from said memory storage device to a remote receiving station.

30. The method to trans-cutaneously monitor analytes of claim 26 wherein:

said bio-compatible implant comprises a fluorophore wherein said bio-compatible implant emits fluorescence of a predetermined wavelength and temporal characteristics, said fluorescence of a predetermined wavelength and temporal characteristics being altered by collisional quenching caused by the presence of a predetermined analyte.

31. The method to trans-cutaneously monitor analytes of claim 26 wherein:

said bio-compatible implant comprises an analyte-free and an analyte-bound form and wherein the ratio of the signals at two excitation or emission wavelengths is used for quantitative measurements.

32. The method to trans-cutaneously monitor analytes of claim 26 wherein:

said bio-compatible implant comprises a fluorescent donor and an analyte-dependent acceptor which spectrally overlaps said fluorescent donor, said bio-compatible implant emitting fluorescence of a predetermined wavelength and temporal characteristics upon absorption of said excitation light emitted from said light emitter, said fluorescence wavelength and temporal characteristics being altered when a predetermined analyte is present.

33. A method to trans-cutaneously monitor analytes, comprising:

synthesizing a modulated electrical output by means of a frequency synthesizer;

inputting said modulated electrical output of said frequency synthesizer means into a light emitting means whereby said light emitting means emits an intensity modulated excitation light, said excitation light having predetermined wavelength and temporal characteristics;

implanting a bio-compatible implant wherein said bio-compatible implant emits fluorescence of a predetermined wavelength and temporal characteristics upon absorption of said excitation light emitted from said light emitter, said fluorescence wavelength and temporal characteristics being altered when a predetermined biologically significant substance is present;

detecting said bio-compatible implant emitted fluorescence of a predetermined wavelength and temporal characteristics by detection means wherein said detection means emits an electrical signal which is directly proportional to the fluorescence wavelength and temporal characteristics received;

comparing said wavelength and temporal characteristics of said excitation light emitted from said light emitting means and said wavelength and temporal characteristics of said fluorescence from said bio-compatible implant;

computing the phase angle difference between said comparison of said light emitted from said light emitting means and said wavelength and temporal characteristics of said fluorescent light from said bio-compatible implant to a quantity of said biologically significant substance present and relating said phase angle difference to the quantity of a biologically significant substance present; and displaying the quantity of said biologically significant substance present.

* * * * *

UNITED STATES PATENT AND TRADEMARK OFFICE
CERTIFICATE OF CORRECTION

PATENT NO. : 5,628,310
DATED : May 13, 1997
INVENTOR(S) : Govind RAO et al

It is certified that error appears in the above-identified patent and that said Letters Patent is hereby corrected as shown below:

Column 25, line 42 (claim 20)

after "of claim" change "20" to -- 19 --

Signed and Sealed this

First Day of July, 1997

Attest:

Attesting Officer

BRUCE LEHMAN

Commissioner of Patents and Trademarks